United States Patent [19]

Fechtig

[11] 4,013,650
[45] Mar. 22, 1977

[54] PROCESS FOR THE MANUFACTURE OF 3-METHYLENE-CEPHAM COMPOUNDS

[75] Inventor: Bruno Fechtig, Reinach, Switzerland

[73] Assignee: Ciba-Geigy Corporation, Ardsley, N.Y.

[22] Filed: Dec. 17, 1973

[21] Appl. No.: 425,343

[30] Foreign Application Priority Data

Jan. 9, 1973    Switzerland ............... 224/73
Mar. 5, 1973    Switzerland ............... 4609/73

[52] U.S. Cl. ................... 260/243 C; 424/246
[51] Int. Cl.² ................................. C07D 501/04
[58] Field of Search ..................... 260/243 C

[56] References Cited
UNITED STATES PATENTS

| | | | |
|---|---|---|---|
| 3,769,277 | 10/1973 | Long et al. | 260/243 C |
| 3,773,761 | 11/1973 | Blackburn et al. | 260/243 C |
| 3,775,408 | 11/1973 | Ochiai et al. | 260/243 C |
| 3,792,995 | 2/1974 | Ochiai et al. | 260/243 C |
| 3,883,518 | 5/1975 | Ponticello et al. | 260/243 C |
| 3,932,393 | 1/1976 | Chauvette | 260/243 C |

Primary Examiner—Nicholas S. Rizzo
Assistant Examiner—Jose Tovar
Attorney, Agent, or Firm—Joseph G. Kolodny; John J. Maitner; Theodore O. Groeger

[57] ABSTRACT

Compounds of the formula

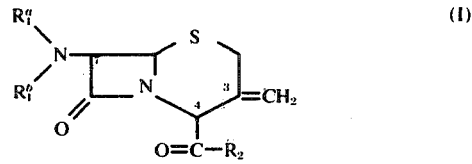

wherein $R_1{}^a$ represents hydrogen or an amino protective group $R_1{}^A$ and $R_1{}^b$ represents hydrogen or an acyl group Ac, or $R_1{}^a$ and $R_1{}^b$ together represent a bivalent amino protective group, and $R_2$ represents hydroxyl or a radical $R_2{}^A$ which together with the carbonyl grouping —C(=O)— forms a protected carboxyl group, as well as 1-oxides thereof, and salts of such compounds with salt-forming groups, are prepared from compounds of the formula

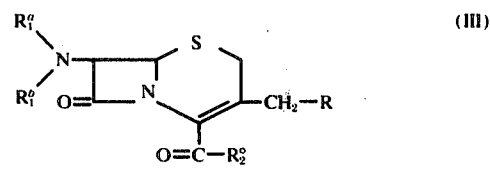

wherein $R_1{}^a$ and $R_1{}^b$ have the above mentioned meaning, R denotes an acyloxy group, $R_2{}^a$ has the meaning of $R_2$ or R and $R_2{}^o$ together denote an epoxy group, from a 1-oxide thereof or a salt of such a compound, by reduction with a metal which has a normal potential of −2.4 to −0.40 volt, or an amalgam thereof, at a pH of 1 to 8, in the presence of water.

10 Claims, No Drawings

PROCESS FOR THE MANUFACTURE OF 3-METHYLENE-CEPHAM COMPOUNDS

The invention relates to a process for the manufacture of 7β-amino-3-methylene-cepham-carboxylic acid compounds of the formula

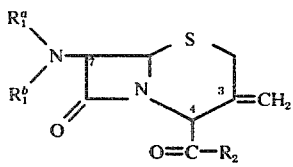

wherein $R_1^a$ represents hydrogen or an amino protective group $R_1^A$, and $R_1^b$ represents hydrogen or an acyl group Ac, or $R_1^a$ and $R_1^b$ together represent a bivalent amino protective group, and $R_2$ represents hydroxyl or a radical $R_2^A$ which together with the carbonyl grouping —C(=O)— forms a protected carboxyl group, as well as 1-oxides thereof, and salts of such compounds with salt-forming groups.

The compounds of the formula I which can be manufactured according to the invention, their 1-oxides or their salts can be used as intermediate products for the manufacture of antibiotically active cephalosporane compounds.

In compounds of the formula I, the optionally protected carboxyl group of the formula —C(=O)—$R_2$ preferably has the α-configuration.

An amino protective group $R_1^A$ is a group which can be replaced by hydrogen, above all an acyl group Ac, also a triarylmethyl group, especially the trityl group, as well as an organic silyl group, and an organic stannyl group. A group Ac above all represents the acyl radical of an organic carboxylic acid, preferably with up to 18 carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid (including formic acid) and the acyl radical of a carbonic acid half-derivative.

A bivalent amino protective group formed by the radicals $R_1^a$ and $R_1^b$ together is, in particular, the bivalent acyl radical of an organic dicarboxylic acid, preferably with up to 18 carbon atoms, above all the diacyl radical of an aliphatic or aromatic dicarboxylic acid, and also the acyl radical of an α-aminoacetic acid which is preferably substituted in the α-position and contains, for example, an aromatic or heterocyclic radical, and wherein the amino group is bonded to the nitrogen atom via a methylene radical which is preferably substituted and, for example, contains two lower alkyl groups, such as methyl groups. The radicals $R_1^a$ and $R_1^b$ can together also represent an organic ylidene radical, such as an aliphatic, cycloaliphatic, cycloaliphatic-aliphatic or araliphatic ylidene radical, preferably with up to 18 carbon atoms.

A protected carboxyl group of the formula —C(=O)—$R_2^A$ is above all an esterified carboxyl group but can also represent an anhydride group, usually a mixed anhydride group, or an optionally substituted carbamoyl or hydrazino carbonyl group.

The group $R_2^A$ can be hydroxyl group etherified by an organic radical, wherein the organic radical preferably contains up to 18 carbon atoms, which together with the —C(=O)— grouping forms an esterified carboxyl group. Examples of such organic radicals are aliphatic, cycloaliphatic, cycloaliphatic-aliphatic, aromatic or araliphatic radicals, especially optionally substituted hydrocarbon radicals of this nature, as well as heterocyclic or heterocyclic-aliphatic radicals.

The group $R_2^A$ can also represent an organic silyloxy radical as well as a hydroxyl group etherified by an organometallic radical, such as an appropriate organic stannyloxy group, especially a silyloxy or stannyloxy group which is substituted by 1 to 3, optionally substituted hydrocarbon radicals, preferably with up to 18 carbon atoms, such as aliphatic hydrocarbon radicals, and optionally by halogen, such as chlorine.

A radical $R_2^A$ which forms, with a —C(=O)— grouping an anhydride group, above all a mixed anhydride group, is in particular an acyloxy radical, wherein acyl represents the corresponding radical of an organic carboxylic acid, preferably with up to 18 carbon atoms, such as of an aliphatic, cycloaliphatic, cycloaliphatic-aliphatic, aromatic or araliphatic carboxylic acid or of a carbonic acid half-derivative, such as of a carbonic acid half-ester.

A radical $R_2^A$ which forms a carbamoyl group with a —C(=O)— grouping is an optionally substituted amino group wherein substituents represent optionally substituted monovalent or bivalent hydrocarbon radicals, preferably with up to 18 carbon atoms, such as optionally substituted monovalent or bivalent aliphatic, cycloaliphatic, cycloaliphatic-aliphatic, aromatic or araliphatic hydrocarbon radicals with up to 18 carbon atoms, also appropriate heterocyclic or heterocyclic-aliphatic radicals with up to 18 carbon atoms and/or functional groups, such as optionally functionally modified, but especially free, hydroxyl and also etherified or esterified hydroxyl, wherein the etherifying or esterifying radicals have, for example, the abovementioned meanings and preferably contain up to 18 carbon atoms, as well as acyl radicals, preferably with up to 18 carbon atoms.

In a substituted hydrazinocarbonyl group of the formula —C(=O)—$R_2^A$, one or both nitrogen atoms can be substituted, possible substitutents being above all optionally substituted monovalent or bivalent hydrocarbon radicals, preferably with up to 18 carbon atoms, such as optionally substituted, monovalent or bivalent aliphatic, cycloaliphatic, cycloaliphatic-aliphatic, aromatic or araliphatic hydrocarbon radicals with up to 18 carbon atoms and also appropriate heterocyclic or heterocyclic-aliphatic radicals with up to 18 carbon atoms and/or functional groups, such as acyl radicals, preferably with up to 18 carbon atoms.

The general concepts used in the preceding and following description have, for example, the following meanings:

An aliphatic radical, including the aliphatic radical of an appropriate organic carboxylic acid, as well as an appropriate ylidene radical, is an optionally substituted monovalent or divalent aliphatic hydrocarbon radical, especially lower alkyl, as well as lower alkenyl or lower alkinyl, and also lower alkylidene which can contain, for example, up to 7, preferably up to 4, carbon atoms. Such radicals can optionally be monosubstituted, disubstituted or polysubstituted by functional groups, for example by free, etherified or esterified hydroxyl or mercapto groups, such as lower alkoxy, lower alkenyloxy; lower alkylenedioxy, optionally substituted phenyloxy or phenyl-lower alkoxy, lower alkylthio or optionally substituted phenylthio or phenyl-lower alkylthio, optionally substituted lower alkoxycarbonyloxy or lower alkanoyloxy, or halogen, also by oxo, nitro, optionally substituted amino, for example lower alkylamino, di-lower alkylamino, lower alkyleneamino, oxa-lower alkyleneamino or aza-lower alkyleneamino, as well as acylamino, such as lower alkanoylamino, optionally substituted carbamoylamino, ureidocarbonylamino or guanidinocarbonylamino, azido, acyl, such as lower alkanoyl or benzoyl, optionally functionally modified carboxyl, such as carboxyl present in the form of a salt, esterified carboxyl, such as lower alkoxycarbonyl, optionally substituted carbamoyl, such as N-lower alkylcarbamoyl or N,N-di-lower alkylcarbamoyl and also optionally substituted ureidocarbonyl or guanidinocarbonyl, or nitrile, optionally functionally modified sulpho, such as sulphamoyl or sulpho present in the form of a salt, or optionally O-monosubstituted or O,O-disubstituted phosphono, wherein substituents represent, for example, optionally substituted lower alkyl, phenyl or phenyl-lower alkyl, it also being possible for unsubstituted or O-monosubstituted phosphono to be in the form of a salt, such as in the form of an alkali metal salt.

A bivalent aliphatic radical, including the appropriate radical of a bivalent aliphatic carboxylic acid, is, for example, lower alkylene or lower alkenylene, which can optionally be monosubstituted, disubstituted or polysubstituted, for example like an aliphatic radical indicated above, and/or be interrupted by heteroatoms, such as oxygen, nitrogen or sulphur.

A cycloaliphatic or cycloaliphatic-aliphatic radical, including the cycloaliphatic or cycloaliphatic-aliphatic radical in an appropriate organic carboxylic acid or an appropriate cycloaliphatic or cycloaliphatic-aliphatic ylidene radical, is an optionally substituted, monovalent or bivalent, cycloaliphatic or cycloaliphatic-aliphatic hydrocarbon radical, for example monocyclic, bicyclic or polycyclic cycloalkyl or cycloalkenyl, and also cycloalkylidene, or cycloalkyl- or cycloalkenyl-lower alkyl or -lower alkenyl, as well as cycloalkyl-lower alkylidene or cycloalkenyl-lower alkylidene, wherein cycloalkyl and cycloalkylidene contains, for example, up to 12 such as 3-8, preferably 3-6, ring carbon atoms, whilst cycloalkenyl possesses, for example, up to 12, such as 3-8, for example 5-8, preferably 5 or 6, ring carbon atoms and 1 to 2 double bonds, and the aliphatic part of a cycloaliphatic-aliphatic radical can contain, for example, up to 7, preferably up to 4, carbon atoms. The above cycloaliphatic or cycloaliphatic-aliphatic radicals can, if desired, be mono-substituted, disubstituted or polysubstituted, for example by optionally substituted aliphatic hydrocarbon radicals, such as by the abovementioned optionally substituted lower alkyl groups or, for example, like the abovementioned aliphatic hydrocarbon radicals, by functional groups.

An aromatic radical, including the aromatic radical of an appropriate carboxylic acid, is an optionally substituted aromatic hydrocarbon radical, for example a monocyclic, bicyclic or polycyclic aromatic hydrocarbon radical, especially phenyl, as well as biphenylyl or naphthyl, which can optionally be monosubstituted, disubstituted or polysubstituted, for example like the abovementioned aliphatic and cycloaliphatic hydrocarbon radicals.

A divalent aromatic radical, for example of an aromatic carboxylic acid, is above all 1,2-arylene, especially 1,2-phenylene, which can optionally be monosubstituted, disubstituted or polysubstituted, for example like the abovementioned aliphatic and cycloaliphatic hydrocarbon radicals.

An araliphatic radical, including the araliphatic radical in an appropriate carboxylic acid, and also an araliphatic ylidene radical, is, for example, an optionally substituted araliphatic hydrocarbon radical, such as an aliphatic hydrocarbon radical which is optionally substituted and possesses, for example, up to three optionally substituted monocyclic, bicyclic or polycyclic aromatic hydrocarbon radicals, and above all represents phenyl-lower alkyl or phenyl-lower alkenyl as well as phenyl-lower alkinyl and also phenyl-lower alkylidene, it being possible for such radicals to contain, for example, 1–3 phenyl groups and to be optionally monosubstituted, disubstituted or polysubstituted in the aromatic and/or aliphatic part, for example like the abovementioned aliphatic and cycloaliphatic radicals.

Heterocyclic groups, including those in heterocyclic-aliphatic radicals, including heterocyclic or heterocyclic-aliphatic groups in appropriate carboxylic acids, are especially monocyclic, as well as bicyclic or polycyclic, azacyclic, thiacyclic, oxacyclic, thiazacyclic, thiadiazacyclic, oxazacyclic, diazacyclic, triazacyclic or tetrazacyclic radicals of aromatic character, and also appropriate partially or wholly saturated heterocyclic radicals and these heterocyclic radicals can optionally be monosubstituted, disubstituted or polysubstituted, for example like the abovementioned cycloaliphatic radicals. The aliphatic part in heterocyclic-aliphatic radicals has, for example, the meaning indicated for the corresponding cycloaliphatic-aliphatic or araliphatic radicals.

The acyl radical of a carbonic acid half-derivative is preferably the acyl radical of an appropriate half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester of carbonic acid which is optionally substituted, for example in the $\alpha$- or $\beta$-position, as well as of a lower alkenyl, cycloalkyl, phenyl or phenyl-lower alkyl half-ester of carbonic acid which is optionally substituted in the organic radical. Acyl radicals of a carbonic acid half-ester are furthermore appropriate radicals of lower alkyl half-esters of carbonic acid, in which the lower alkyl part contains a heterocyclic group, for example one of the abovementioned heterocyclic groups of aromatic character, and both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

An etherified hydroxyl group is above all optionally substituted lower alkoxy, wherein substituents above all represent free or functionally modified, such as etherified or esterified, hydroxyl groups, especially lower alkoxy or halogen, also lower alkenyloxy, cycloalkyloxy or optionally substituted phenyloxy, as well as heterocyclyloxy or heterocyclyl-lower alkoxy, especially also optionally substituted phenyl-lower alkoxy.

An optionally substituted amino group is, for example, amino, lower alkylamino, di-lower alkylamino, lower alkyleneamino, oxa-lower alkyleneamino, thia-lower alkyleneamino, aza-lower alkyleneamino, hydroxyamino, lower alkoxyamino, lower alkanoyloxyamino, lower alkoxycarbonylamino or lower alkanoylamino.

An optionally substituted hydrazino group is, for example, hydrazino, 2-lower alkylhydrazino, 2,2-di-lower alkylhydrazino, 2-lower alkoxycarbonylhydrazino or 2-lower alkanoylhydrazino.

Lower alkyl is, for example, methyl, ethyl n-propyl, isopropyl, n-butyl, isobutyl, sec.-butyl or tert.-butyl, as well as n-pentyl, isopentyl, n-hexyl, isohexyl or n-heptyl, whilst lower alkenyl can, for example, be vinyl, allyl, isopropenyl, 2- or 3-methallyl or 3-butenyl, lower alkinyl can, for example, be propargyl or 2-butinyl and lower alkylidene can, for example, be isopropylidene or isobutylidene.

Lower alkylene is, for example, 1,2-ethylene, 1,2- or 1,3-propylene, 1,4-butylene, 1,5-pentylene or 1,6-hexylene, whilst lower alkenylene is, for example, 1,2-ethenylene or 2-buten-1,4-ylene. Lower alkylene interrupted by hetero-atoms is, for example, oxa-lower alkylene, such as 3-oxa-1,5-pentylene, thio-lower alkylene, such as 3-thia-1,5-pentylene, or aza-lower alkylene, such as 3-lower alkyl-3-aza-1,5-pentylene, for example 3-methyl-3-aza-1,5-pentylene.

Cycloalkyl is, for example, cyclopropyl, cyclobutyl, cyclopentyl, cyclohexyl or cycloheptyl as well as adamantyl, whilst cycloalkenyl is, for example, cyclopropenyl, 1-, 2- or 3-cyclopentenyl, 1-, 2- or 3-cyclohexenyl, 3-cycloheptenyl or 1,4-cyclohexadienyl and cycloalkylidene is, for example, cyclopentylidene or cyclohexylidene. Cycloalkyl-lower alkyl or -lower alkenyl is, for example, cyclopropyl-, cyclopentyl-, cyclohexyl- or cycloheptyl-methyl, -1,1- or -1,2-ethyl, -1,1-, -1,2- or -1,3-propyl, -vinyl or -allyl, whilst cycloalkenyl-lower alkyl or -lower alkenyl represents, for example, 1-, 2- or 3-cyclopentenyl-, 1-, 2- or 3-cyclohexenyl- or 1-, 2- or 3-cycloheptenyl-methyl, -1,1- or -1,2-ethyl, -1,1-,-1,2- or -1,3-propyl, -vinyl or -allyl. Cycloalkyl-lower alkylidene is, for example, cyclohexylmethylene, and cycloalkenyl-lower alkylidene is, for example, 3-cyclohexenylmethylene.

Naphthyl is 1- or 2-naphthyl, whilst biphenylyl represents, for example, 4-biphenylyl.

Phenyl-lower alkyl or phenyl-lower alkenyl is, for example, benzyl, 1- or 2-phenylethyl, 1-, 2- or 3-phenyl-propyl, diphenylmethyl, trityl, styryl or cinnamyl, naphthyl-lower alkyl is, for example, 1- or 2-naphthylmethyl and phenyl-lower alkylidene is, for example, benzylidene.

Heterocyclic radicals are above all optionally substituted heterocyclic radicals of aromatic character, for example appropriate monocyclic, monoazacyclic, monothiacyclic or monooxacylic radicals, such as pyrryl, for example 2-pyrryl or 3-pyrryl, pyridyl, for example 2-, 3- or 4-pyridyl and also pyridinium, thienyl, for example 2- or 3-thienyl, or furyl, for example 2-furyl bicyclic monoazacyclic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, oxazacyclic, thiazacyclic or thiadiazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazoyl, thiazolyl, for example 2-thiazolyl, isothiazolyl, for example 3- or 4-isothiazolyl, or 1,2,4- or 1,3,4-thiadiazolyl, for example 1,2,4-thiadiazol-3-yl or 1,3,4-thiadiazolyl,-2-yl, or bicyclic diazacyclic, oxazacyclic or thiazacyclic radicals, such as benzimidazolyl, for example 2-benzimidazolyl, benzoxazolyl, for example 2-benzoxazolyl, or benzthiazolyl, for example 2-benzthiazolyl. Appropriate partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are lower alkyl or lower alkenyl containing heterocyclic groups, especially those mentioned above. The abovementioned heterocyclic radicals can be substituted, for example by optionally substituted aliphatic hydrocarbon radicals, especially lower alkyl, such as methyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentoxy or tert.-pentoxy. These groups can be substituted, for example as in halogen-lower alkoxy, especially 2-halogen-lower alkoxy, for example 2,2,2-trichloroethoxy, 2-chloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylidenedioxy, cycloalkoxy is, for example, cyclopentyloxy, cyclohexyloxy or adamantyloxy, phenyl-lower alkoxy is, for example, benzyloxy, 1- or 2-phenylethoxy, diphenylmethoxy or 4,4'-dimethoxydiphenylmethoxy or heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio or n-butylthio, lower alkenylthio is, for example, allylthio, and phenyl-lower alkylthio is, for example, benzylthio, whilst mercapto groups etherified by heterocyclic radicals or heterocyclyl-aliphatic radicals are especially pyridylthio, for example 4-pyridylthio, imidazolylthio, for example 2-imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, as well as lower alkanoyloxy, for example acetoxy or propionyloxy, lower alkoxycarbonyloxy, for example methoxycarbonyloxy, ethoxycarbonyloxy or tert.-butoxycarbonyloxy, 2-halogeno-lower alkoxycarbonyloxy, for example 2,2,2-trichloroethoxycarbonyloxy, 2-bromoethoxycarbonyloxy or 2-iodoethoxycarbonyloxy, or arylcarbonylmethoxycarbonyloxy, for example phenacyloxycarbonyloxy.

Lower alkoxycarbonyl is, for example, methoxycarbonyl, ethoxycarbonyl, n-propoxycarbonyl, isopropoxycarbonyl, tert.-butoxycarbonyl or tert.-pentoxycarbonyl.

N-Lower alkyl- or N,N-di-lower alkyl-carbamoyl is, for example, N-methylcarbamoyl, N-ethylcarbamoyl. N,N-dimethylcarbamoyl or N,N-diethylcarblamoyl, whilst N-lower alkylsulphamoyl represents, for example, N-methylsulphamoyl or N,N-dimethylsulphamoyl.

A carboxyl or sulpho present in the form of an alkali metal salt is, for example, a carboxyl or sulpho present in the form of a sodium or potassium salt.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, thia-lower alkyleneamino is, for example, thiomorpholino, and aza-lower alkyleneamino is, for example piperazino or 4-methylpiperazino. Acylamino in particular represents carbamoylamino, lower alkylcarbamoylamino, such as methylcarbamoylamino, ureidocarbonylamino, guanidinocarbonylamino, lower alkoxycarbonylamino, for example methoxycarbonylamino, ethoxycarbonylamino or tert.-butoxycarbonylamino, lower alkanoylamino, such as acetylamino or propionylamino, and also phthalimido, or sulphoamino optionally present in the form of a salt, such as in the form of an alkali metal salt, for example in the form of a sodium salt or ammonium salt.

Lower alkanoyl is, for example, formyl, acetyl, propionyl or pivaloyl. O-Lower alkyl-phosphono is, for example, O-methyl- or O-ethyl-phosphono, O,O-di-lower alkyl-phosphono is, for example, O,O-dimethyl-phosphono or O,O-dimethylphosphono, O-phenyl-lower alkyl-phosphono is, for example, O-benzyl-phosphono, and O-lower alkyl-O-phenyl-lower alkyl-phosphono is, for example, O-benzyl-O-methyl-phosphono.

Lower alkenyloxycarbonyl is, for example, vinyloxycarbonyl, whilst cycloalkoxycarbonyl and phenyl-lower alkoxycarbonyl represent, for example, adamantyloxycarbonyl, benzyloxycarbonyl, 4-methoxy-benzyloxycarbonyl, diphenylmethoxycarbonyl or α-4-biphenylyl-α-methyl-ethoxycarbonyl. Lower alkoxycarbonyl, wherein lower alkyl contains, for example, a monocyclic, monoazacyclic, monooxacyclic or monothiacyclic group, is, for example, furyl-lower alkoxycarbonyl, such as furfuryloxycarbonyl, or thienyl-lower alkoxycarbonyl, such as 2-thenyloxycarbonyl.

2-Lower alkylhydrazino and 2,2-di-lower alkylhydrazino is, for example, 2-methylhydrazino or 2,2-dimethylhydrazino, 2-lower alkoxycarbonylhydrazino is, for example 2-methoxycarbonylhydrazino, 2-ethoxycarbonylhydrazino or 2-tert.-butoxycarbonylhydrazino and lower alkanoylhydrazino is, for example, 2-acetylhydrazino.

An acyl group Ac in particular represents an acyl radical of an organic carboxylic acid, preferably with up to 18 carbon atoms, contained in a naturally occurring or biosynthetically, semi-synthetically or total-synthetically obtainable, preferably pharmaceutically active, N-acyl derivative of a 6-amino-penam-3-carboxylic acid compound or 7-amino-3-cephem-4-carboxylic acid compound, or represents an easily removable acyl radical, especially of a carbonic acid half-derivative.

An acyl radical Ac contained in a pharmacologically active N-acyl derivative of a 6-amino-penam-3-carboxylic acid compound or 7-amino-3-cephem-4-carboxylic acid compound is above all a group of the formula

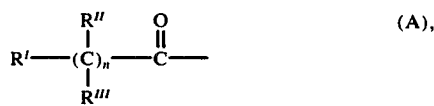

wherein $n$ represents O and $R^I$ denotes hydrogen or an optionally substituted cycloaliphatic or aromatic hydrocarbon radical or an optionally substituted heterocyclic radical, preferably of aromatic character, a functionally modified, for example esterified or etherified, hydroxyl or mercapto group or an optionally substituted amino group, or wherein $n$ represents 1, $R^I$ represents hydrogen or an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character and/or a quaternary nitrogen atom, an optionally functionally modified, preferably etherified or esterified, hydroxyl or mercapto group, an optionally functionally modified carboxyl group, an acyl group, an optionally substituted amino group or an azido group and each of the radicals $R^{II}$ and $R^{III}$ denotes hydrogen, or wherein $n$ represents 1, $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably has aromatic character, $R^{II}$ denotes an optionally functionally modified, for example esterified or etherified, hydroxyl or mercapto group, an optionally substituted amino group, an optionally functionally modified carboxyl or sulpho group, an optionally O-monosubstituted or O-disubstituted phosphono group, an azido group or a halogen atom and $R^{III}$ represents hydrogen, or wherein $n$ represents 1, each of the radicals $R^I$ and $R^{II}$ denotes a functionally modified, preferably etherified or esterified, hydroxyl group or an optionally functionally modified carboxyl group, and $R^{III}$ represents hydrogen, or wherein $n$ represents 1, $R^I$ denotes hydrogen or an optionally substituted aliphatic, cycloaliphatic, cycloaliphatic-aliphatic, aromatic or araliphatic hydrocarbon radical and $R^{II}$ and $R^{III}$ together represent an optionally substituted aliphatic, cycloaliphatic, cycloaliphatic-aliphatic or araliphatic hydrocarbon radical which is bonded to the carbon atom by a double bond, or wherein $n$ represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

In the abovementioned acyl groups of the formula A, for example, $n$ represents O and $R^I$ represents hydrogen or a cycloalkyl group with 5–7 ring carbon atoms which is optionally substituted, preferably in the 1-position, by optionally protected amino, such as amino, acylamino, wherein acyl above all represents the acyl radical of a carbonic acid half-ester, such as lower alkoxycarbonyl, 2-halogeno-lower alkoxycarbonyl or phenyl-lower alkoxycarbonyl radical, or a sulphoamino group which is optionally present in the form of a salt, for example in the form of an alkali metal salt, a phenyl, naphthyl or tetrahydronaphthyl group which is optionally substituted, preferably by hydroxyl, lower alkoxy, for example methoxy, acyloxy, wherein acyl above all represents the acyl radical of a carbonic acid half-ester, such as a lower alkoxycarbonyl, 2-halogeno-lower alkoxycarbonyl or phenyl-lower alkoxycarbonyl radical, and/or halogen, for example chlorine, a heterocyclic group which is optionally substituted, for example by lower alkyl, for example methyl and/or phenyl, which can in turn carry substituents, such as halogen, for example chlorine, such as a 4-isoxazolyl group, or an amino group which is preferably N-substituted, for example by an optionally substituted lower alkyl radical, such as a lower alkyl radical containing halogen, for example chlorine, or $n$ represents 1, $R^I$ represents a lower alkyl group which is optionally substituted, preferably by halogen, such as chlorine, by phenyloxy which is optionally substituted, such as phenyloxy containing hydroxyl, acyloxy, wherein acyl has the above-mentioned meaning, and/or halogen, for example chlorine, or by optionally protected amino and/or carboxyl, for example a 3-amino-3-carboxy-propyl radical having an optionally protected amino and/or carboxyl group, for example a silylated amino or acylamino, such as lower alkanoylamino or halogeno-lower alkanoylamino group, and/or silylated or esterified carboxyl group, or represents a lower alkenyl group, a phenyl group which is optionally substituted, such as a phenyl group which optionally contains acylated hydroxyl and/or halogen, for example chlorine, and also optionally protected, such as acylated, amino-lower alkyl, such as aminomethyl, or optionally substituted phenyloxy, such as phenyloxy which possesses optionally acylated hydroxyl and/or halogen, for example chlorine, or represents a pyridyl, pyridinium, thienyl, 1-imidazolyl or 1-tetrazolyl group which is substituted by optionally protected, such as acylated, amino or aminomethyl, or represents an optionally substituted lower alkoxy group, for example methoxy group, a phenyloxy group which is optionally substituted, for example by optionally acylated hydroxyl and/or halogen, such as chlorine, or represents a lower alkylthio group, for example n-butylthio group, or lower alkenylthio group, for example allylthio group, a phenylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadiazol-3-ylthio, 1,3,4-thiadiazol-2-ylthio, such as 5-methyl-1,3,4-thiadiazol-2-ylthio, or 5-tetrazolylthio, such as 1-methyl-5-tetrazolylthio group, which are optionally substituted, for example by lower alkyl, such as methyl, or represents a halogen atom, especially chlorine or bromine atom, an optionally functionally modified carboxyl group, such as lower alkoxycarbonyl, for example methoxycarbonyl or ethoxycarbonyl, nitrile or carbamoyl which is optionally N-substituted, for example by lower alkyl, such as methyl, or phenyl, or represents an optionally substituted lower alkanoyl group, for example an acetyl or propionyl group, or benzoyl group, or an azido group, and $R^{II}$ and $R^{III}$ represents hydrogen, or $n$ represents 1, $R^I$ represents a phenyl, furyl, thienyl or 4-isothiazolyl group which is optionally substituted, for example by hydroxyl which is optionally acylated, and/or by halogen, for example chlorine, and also represents a 1,4-cyclohexadienyl group, $R^{II}$ represents optionally protected or substituted amino, for example acylated acylamino, such as lower alkoxycarbonylamino, 2-halogeno-lower alkoxycarbonylamino or phenyl-lower alkoxycarbonylamino, for example tert.-butoxycarbonylamino, 2,2,2-trichloroethyoxycarbonylamino or diphenylmethyloxycarbonylamino, tritylamino, or optionally substituted carbamoylamino, such as guanidinocarbonylamino, or a sulphoamino group which is optionally present in the form of a salt, for example in the form of an alkali metal salt, an azido group, a carboxyl group which is optionally present in the form of a salt, for example in the form of an alkali metal salt, or in an esterified form, for example as a lower alkoxycarbonyl group, for example methoxycarbonyl group or ethoxycarbonyl group, a nitrile group, a sulpho group, an optionally functionally modified hydroxyl group, in particular acyloxy, such as formyloxy, as well as lower alkoxycarbonyloxy, 2-halogeno-lower alkoxycarbonyloxy or phenyl-lower alkoxycarbonyloxy, for example tert.-butoxycarbonyloxy, 2,2,2-trichlorocarbonyloxy or diphenylmethoxycarbonyloxy, or optionally substituted lower alkoxy or phenyloxy, an O-lower alkyl-phosphono group or O,O-di-lower alkyl-phosphono group, for example O-methyl-phosphono or O,O-dimethylphosphono, or a halogen atom, for example chlorine or bromine, and $R^{III}$ represent hydrogen, or $n$ represents 1, $R^I$ and $R^{II}$ each represent halogen, for example bromine, or lower alkoxycarbonyl, for example methoxycarbonyl, and $R^{III}$ represents hydrogen, or $n$ represents 1, $R^I$ represents a phenyl, furyl, thienyl or 4-isothiazolyl group, which are optionally substituted, for example by hydroxyl which is optionally acylated, and/or by halogen, for example chlorine, and also represents a 1,4-cyclohexadienyl group, $R^{II}$ represents aminomethyl which is optionally protected, for example as indicated above, and $R^{III}$ represents hydrogen, or $n$ represents 1 and each of the groups $R^I$, $R^{II}$ and $R^{III}$ represents lower alkyl, for example methyl.

Such acyl radicals Ac are, for example, formyl, cyclopentylcarbonyl, α-aminocyclopentylcarbonyl or α-aminocyclohexylcarbonyl (with an optionally substituted amino group, for example a sulphoamino group optionally present in the form of a salt, or an amino group which is substituted by an acyl radical which can be split off, preferably easily, for example on treatment with an acid agent, such as trifluoroacetic acid, or by treatment with a chemical reducing agent, such as zinc in the presence of aqueous acetic acid, or an acyl radical which can be converted into such a radical, preferably a suitable acyl radical of a carbonic acid half-ester, such as 2,2,2-trichloroethoxycarbonyl, 2-bromoethoxycarbonyl, 2-iodoethoxycarbonyl, tert. butoxycarbonyl or phenacyloxycarbonyl, or of a carbonic acid half-amide, such as carbamoyl or N-methylcarbamoyl, as well as by trityl), 2,6-dimethoxybenzoyl, tetrahydronaphthoyl, 2-methoxy-naphthoyl, 2-ethoxy-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, pivaloyl, hexanoyl, octanoyl, acrylyl, crotonoyl, 3-butenoyl, 2-pentenoyl, methoxyacetyl, butylthioacetyl, allylthioacetyl, methylthioacetyl, chloroacetyl, bromoacetyl, dibromoacetyl, 3-chloropropionyl, 3-bromopropionyl, aminoacetyl or 5-amino-5-carboxyvaleryl (with an amino group which is optionally substituted, for example as indicated, such as substituted by a monoacyl or diacyl radical, for example an optionally halogenated lower alkanoyl radical, such as acetyl or dichloroacetyl, or phthaloyl, and/or with an optionally functionally modified carboxyl group, for example a carboxyl group present in the form of a salt, such as a sodium salt, or in the form of an ester, such as a lower alkyl ester, for example methyl or ethyl ester, or an aryl-lower alkyl ester, for example diphenylmethyl ester), azidoacetyl, carboxyacetyl, methoxycarbonylacetyl, ethoxycarbonylacetyl, bis-methoxycarbonylacetyl, N-phenylcarbamoylacetyl, cyanoacetyl, α-cyanopropionyl, 2-cyano-3,3-dimethyl-acrylyl, phenylacetyl, α-bromophenylacetyl, α-azido-phenylacetyl, 3-chlorophenylacetyl, 4-aminomethylphenyl-acetyl (with an amino group which is optionally substituted, for example, as indicated), phenacylcarbonyl, phenoxyacetyl, 4-trifluoromethylphenoxyacetyl, benzyloxyacetyl, phenylthioacetyl, bromophenylthioacetyl, 2-phenoxypropionyl, α-phenoxyphenylacetyl, α-methoxyphenylacetyl, α-ethoxy-phenylacetyl, α-methoxy-3,4-dichlorophenylacetyl, α-cyano-phenylacetyl, especially phenylglycyl, 4-hydroxyphenylglycyl, 3-chloro-4-hydroxyphenylglycyl, 3,5-dichloro-4-hydroxy-phenylglycyl, α-aminomethyl-α-phenylacetyl or α-hydroxyphenylacetyl, (it being possible, in these radicals, for an amino group which is present to be optionally substituted, for example as indicated above, and/or an aliphatic and/or phenolically bonded hydroxyl group which is present to be optionally protected, analogously to the amino group, for example by a suitable acyl radical, especially by formyl or by an acyl radical of a carbonic acid half-ester), or α-O-methyl-phosphonophenylacetyl or α-O,O-dimethyl-phosphono-phenylacetyl, also benzylthioacetyl, benzylthiopropionyl, α-carboxyphenylacetyl (with a carboxyl group which is optionally functionally modified, for example as indicated above), 3-phenylpropionyl, 3-(3-cyanophenyl)-propionyl, 4-(3-methoxyphenyl)-butyryl, 2-pyridylacetyl, 4-amino-pyridiniumacetyl (optionally with an amino group which is substituted, for example as indicated above), 2-thienylacetyl, 3-thienylacetyl, 2-tetrahydrothienylacetyl, 2-furylacetyl, 1-imidazolylacetyl, 1-tetrazolylacetyl, α-carboxy-2-thienylacetyl or α-carboxy-3-thienylacetyl (optionally with a carboxyl group which is functionally modified, for example as indicated above), α-cyano-2-thienylacetyl, α-amino-α-(2-thienyl)-acetyl, α-amino-α-(2-furyl)acetyl or α-amino-α-(4-isothiazolyl)-acetyl (optionally with an amino group which is substituted, for example as indicated above), α-sulphophenylacetyl (optionally with a sulpho group which is functionally modified, for example like the carboxyl group), 3-methyl-2-imidazolylthioacetyl, 1,2,4-triazol-3-ylthioacetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl.

An easily removable acyl radical Ac, especially of a carbonic acid half-ester, is above all an acyl radical of a half-ester of carbonic acid which can be split off by reduction, for example on treatment with a chemical reducing agent, or by treatment with acid, for example with trifluoroacetic acid, such as a lower alkoxycarbonyl group which preferably has multiple branching and/or an aromatic substituent on the carbon atom in the α-position to the oxy group, or a methoxycarbonyl group which is substituted by arylcarbonyl, especially benzoyl, radicals, or a lower alkoxycarbonyl radical which is substituted in the β-position by halogen atoms, for example tert.-butoxycarbonyl, tert.-pentoxycarbonyl, phenacyloxycarbonyl, 2,2,2-trichloroethoxycarbonyl or 2-iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyl-lower alkoxycarbonyl, such as 4-methoxyphenyl-methoxycarbonyl, above all α-phenyl-lower alkoxycarbonyl, wherein the α-position is preferably polysubstituted, for example diphenylmethoxycarbonyl or α-4-biphenylyl-α-methylethoxycarbonyl, or furyl-lower alkoxycarbonyl, above all α-furyl-lower alkoxycarbonyl, for example furfuryloxycarbonyl.

A bivalent acyl group formed by the two radicals $R_1^A$ and $R_1^b$ is, for example, the acyl radical of a lower alkanedicarboxylic acid or lower alkenedicarboxylic acid, such as succinyl, or of an o-arylenedicarboxylic acid, such as phthaloyl.

A further bivalent radical formed by the groups $R_1^A$ and $R_1^b$ is, for example, a 1-oxo-3-aza-1,4-butylene radical which is substituted, especially in the 2-position and contains, for example, optionally substituted phenyl or thienyl, and is optionally monosubstituted or disubstituted by lower alkyl, such as methyl, in the 4-position, for example 4,4-dimethyl-2-phenyl-1-oxo-3-aza-1,4-butylene.

An etherified hydroxyl group $R_2^4$ forms, together with the carbonyl grouping, an esterified carboxyl group which can preferably be split easily or can be converted easily into another functionally modified carboxyl group, such as into a carbamoyl or hydrazinocarbonyl group. Such a group $R_2^4$ is, for example, lower alkoxy, such as methoxy, ethoxy, n-propoxy or isopropoxy, which, together with the carbonyl grouping, forms an esterified carboxyl group, which can easily be converted, especially in 2-cephem compounds, into a free carboxyl group or into another functionally modified carboxyl group.

An etherified hydroxyl group $R_2^4$ which together with a —C(=O)— grouping forms an esterified carboxyl group which can be split particularly easily represents, for example, 2-halogeno-lower alkoxy, wherein halogen preferably has an atomic weight above 19. Such a radical forms, together with the —C(=O)— grouping, an esterified carboxyl group which can easily be split on treatment with chemical reducing agents under neutral or weakly acid conditions, for example with zinc in the presence of aqueous acetic acid, or an esterified carboxyl group which can easily be converted into such a group and is, for example, 2,2,2-trichloroethoxy or 2-iodoethoxy, also 2-chloroethoxy or 2-bromoethoxy, which can easily be converted into the latter.

An etherified hydroxy group $R_2^4$ which together with the —C(=O)— grouping represents an esterified carboxyl group which can also be split easily on treatment with chemical reducing agents under neutral or weakly acid conditions, for example on treatment with zinc in the presence of aqueous acetic acid, and also on treatment with a suitable nucleophilic reagent, for example sodium thiophenolate, is an arylcarbonylmethoxy group, wherein aryl in particular represents an optionally substituted phenyl group, and preferably phenacyloxy.

The group $R_2^4$ can also represent an arylmethoxy group wherein aryl in particular denotes a monocyclic, preferably substituted, aromatic hydrocarbon radical. Such a radical forms, together with the —C(=O)— grouping, an esterified carboxyl group which can easily be split on irradiation, preferably with ultraviolet light, under neutral or acid conditions. An aryl radical in such an arylmethoxy group in particular contains as substituents lower alkoxy, for example methoxy, (which in the preferred phenyl radical are above all in the 3-, 4- and/or 5-position) and/or above all nitro (preferably in the 2-position in the preferred phenyl radical). Such radicals are above all 3- or 4-methoxybenzyloxy, 3,5-dimethoxy-benzyloxy, 2-nitro-benzyloxy or 4,5-dimethoxy-2-nitro-benzyloxy).

An etherified hydroxy group $R_2^A$ can also represent a radical which, together with the —C(=O)— grouping, forms an esterified carboxyl group which can easily be split under acid conditions, for example on treatment with trifluoroacetic acid or formic acid. Such a radical is above all a methoxy group in which methyl is polysubstituted by optionally substituted hydrocarbon radicals, especially aliphatic or aromatic hydrocarbon radicals, such as lower alkyl, for example methyl or phenyl, or is monosubstituted by a carbocyclic aryl group possessing electron-donating substituents or by a heterocyclic group of aromatic character possessing oxygen or sulphur as a ring member, or in which methyl denotes a ring member in a polycycloaliphatic hydrocarbon radical or denotes the ring member which represents the α-position to the oxygen or sulphur atom in an oxacycloaliphatic or thiacycloaliphatic radical.

Preferred polysubstituted methoxy groups of this nature are tert.-lower alkoxy, for example tert.-butoxy or tert.-pentoxy, optionally substituted diphenylmethoxy, for example diphenylmethoxy or 4,4'-dimethoxy-diphenylmethoxy, and also 2-(4-biphenylyl)-2-propoxy, whilst a methoxy group which contains the abovementioned substituted aryl group or the heterocyclic group is, for example, an α-lower alkoxy-phenyl-lower alkoxy, such as 4-methoxybenzyloxy or 3,4-dimethoxybenzyloxy, or furfuryloxy, such as 2-furfuryloxy. A polycycloaliphatic hydrocarbon radical in which the methyl of the methoxy group represents a branched, preferably triply branched, ring member, is, for example, adamantyl, such as 1-adamantyl, and an abovementioned oxacycloaliphatic or thiacycloaliphatic radical wherein the methyl of the methoxy group is the ring member which represents the α-position to the oxygen atom or sulphur atom, denotes, for example, 2-oxa- or 2-thia-lower alkylene or -lower alkenylene with 5–7 ring atoms, such as 2-tetrahydrofuryl, 2-tetrahydropropyranyl (sic) or 2,3-dihydro-2-pyranyl or corresponding sulphur analogues.

The radical $R_2^A$ can also represent an etherified hydroxyl group which, together with the —C(=O)— grouping forms an esterified carboxyl group which can be split hydrolytically, for example under weakly basic or weakly acid conditions. Such a radical is, preferably, an etherified hydroxyl group which forms an activated ester group with the —C(=O)— grouping, such as nitrophenyloxy, for example 4-nitrophenyloxy or 2,4-dinitrophenyloxy, nitrophenyl-lower alkoxy, for example 4-nitro-benzyloxy, polyhalogenophenyloxy, for example 2,4,6-trichlorophenyloxy or 2,3,4,5,6-pentachlorophenyloxy, and also cyanomethoxy, as well as acylaminomethoxy, for example phthaliminomethoxy or succinyliminomethoxy.

The group $R_2^A$ can also represent an etherified hydroxyl group which, together with the carboxyl grouping of the formula —C(=O)—, forms an esterified carboxyl group which can be split under hydrogenolytic conditions and is, for example, α-phenyl-lower alkoxy, which is optionally substituted, for example by lower alkoxy or nitro, such as benzyloxy, 4-methoxybenzyloxy or 4-nitrobenzyloxy.

The group $R_2^A$ can A be an etherified hydroxyl group which, together with the carbonyl grouping —C(=O)—, forms an etherified carboxyl group which can be split under physiological conditions, above all lower alkanoyloxymethoxy, for example acetoxymethoxy or pivaloyloxymethoxy.

A silyloxy or stannyloxy group $R_2^A$ preferably contains optionally substituted aliphatic, cycloaliphatic, aromatic or araliphatic hydrocarbon radicals, such as lower alkyl, cycloalky, phenyl or phenyl-lower alkyl groups, and above all represents tri-lower alkylsilyloxy, for example trimethylsilyloxy, or tri-lower alkylstannyloxy, for example tri-n-butylstannyloxy.

An acyloxy radical $R_2^A$ which, together with a —C(=O)— grouping, forms a mixed anhydride group which can be split, preferably hydrolytically, contains, for example, the acyl radical of one of the abovementioned organic carboxylic acids or carbonic acid half-derivatives and is, for example, lower alkanoyloxy, for example acetoxy, or lower alkoxycarbonyloxy, for example ethoxycarbonyloxy.

A radical $R_2^A$ which, together with a —C(=O)— grouping, forms an optionally substituted carbamoyl or hydrazinocarbonyl group is, for example, amino, lower alkylamino or di-lower alkylamino, such as methylamino, ethylamino, dimethylamino or diethylamino, lower alkyleneamino, for example pyrrolidino or piperidino, oxa-lower alkyleneamino, for example morpholino, hydroxylamino, hydrazino, 2-lower alkyl-hydrazino or 2,2-dimethylhydrazino.

Salts are, in particular, those of compounds of the formula I having an acid grouping such as a carboxyl, sulpho or phosphono group, above all metal salts or ammonium salts, such as alkali metal salts and alkaline earth metal salts, for example sodium, potassium, magnesium or calcium salts, as well as ammonium salts with ammonia or suitable organic amines, possible amines for the salt formation being, above all, aliphatic, cycloaliphatic, cycloaliphatic-aliphatic and araliphatic primary, secondary or tertiary monoamines, diamines or polyamines, as well as heterocyclic bases, such as lower alkylamines, for example triethylamine, hydroxylower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine, or benzylamines, for example N,N'-dibenzyl-ethylenediamine, and also bases of the pyridine type, for example pyridine, collidine or quinoline. Compounds of the formula I which possess a basic group can also form acid addition salts, for example with inorganic acids, such as hydrochloric acid, sulphuric acid or phorsphoric acid, or with suitable organic carboxylic acids or sulphonic acids, for example trifluoroacetic acid. Compounds of the formula I having a acid group and a basic group can also be in the form of inner salts, that is to say in the form of a zwitter-ion.

Salts of compounds of the formula I with an acid grouping, which are derived from the cations used in the manufacturing process according to the invention or the cations formed during the reaction, deserve particular mention.

Some compounds falling under the formula I, as well as 1-oxide and salts thereof, and processes for their maufacture, are already known. Thus, such compounds can be manufactured by reducing a 7-amino- or 7-acylamino-3-acetoxymethyl-3-cephem-4-carboxylic acid according to Netherlands Laid-Open Specification No. 71/16,873 with a chromium-II compound or a 3-thio-substituted 7-amino- or 7-acylamino-3-thiomethyl-3-cephem-4-carboxylic acid compound according to German Offenlegungsschrift No. 2,209,020 by means of molecular hydrogen in the presence of a metallic hydrogenation catalyst, or with nascent hydrogen. However, both methods are technically not entirely satisfactory in that only moderate yields are obtained. Furthermore, because of longer reaction times or because of the use of elevated temperatures, 7-amino- or 7-acylamino-3-methyl-3-cephem-4-carboxylic acid derivatives and, in some cases, also the corresponding 3-methyl-2-cephem derivatives are formed as by-products which must be removed from the reaction mixture by chromatography. In the process according to the Netherlands Laid-Open Specification, the formation of chromium complexes in addition has an unfavourable effect on the yield. A further disadvantage of the method according to the German Offenlegungsschrift if that the manufacture of the thio-substituted starting materials from the natural easily accessible 3-acetoxymethyl-3-cephem-4-carboxylic acid derivatives implies an additional synthesis step.

It follows from the abovementioned publications that 7β-amino-3-methylene-cephem-4-carboxylic acid compounds of the formula I themselves possess little or no antibiotic properties but that they can, on the other hand, be isomerised to the valuable 7β-amino-3-methyl-3-cephem-4-carboxylic acid compounds. Such 3-methyl compounds, for example cephalexin (7β-(D-α-aminophenyl-acetamido)-desacetoxy-cephalosporanic acid), have excellent antibiotic properties even on oral administration and can therefore be used for the treatment of various bacterial infection in man and animals.

Compounds of the formula I as well as their 1-oxides can furthermore be used as intermediate products for the manufacture of valuable 3-oxo-cepham compounds as well as 3-hydroxy and 3-substituted hydroxy-3-cephem compounds. Amongst these, particularly valuable compounds are those of the formula

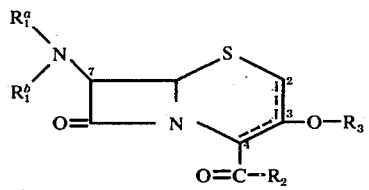

(II)

wherein $R_1^a$, $R_1^b$ and $R_2$ have the abovementioned meaning and $R_3$ represents an optionally substituted hydrocarbon radical or an acyl group, and which contain a double bond in the 2,3- or in the 3,4-position, as well as 1-oxides of compounds of the formula II wherein the double bond is in the 3,4-position, or salts of such compounds having salt-forming groups.

The enol derivatives of the formula II are ethers and esters of 2-cephem-3-ol and 3-cephem-3-ol compounds.

In 2-cephem compounds of the formula II with a double bond in the 2,3,-position, the optionally protected carboxyl group of the formula $—C(=O)—R_2$ preferably has the α-configuration.

An optionally substituted hydrocarbon radical $R_3$ is preferably a corresponding cycloaliphatic or cycloaliphatic-aliphatic hydrocarbon radical, but especially an optionally substituted aliphatic hydrocarbon radical and also a corresponding aralophatic hydrocarbon radical. An acyl group $R_3$ is in the first place the acyl radical of an organic carboxylic acid, including formic acid, such as the acyl radical of a cycloaliphatic, cycloaliphatic-aliphatic, araliphatic, heterocyclic or heterocyclic-aliphatic carboxylic acid, especially the acyl radical of an aliphatic carboxylic acid, or of an aromatic carboxylic acid as well as of a carboxylic acid half-derivative.

An optionally substituted aliphatic hydrocarbon radical $R_3$ is, in particular, lower alkyl with up to 7, preferably with up to 4 carbon atoms, such as ethyl, n-propyl, isopropyl or n-butyl, and above all methyl, and also lower alkenyl, of for example allyl, tert.-amino-lower alkyl, wherein the tert.-amino group is separated from the oxygen atom by at least two carbon atoms, such as 2- or 3-di-lower alkylamino-lower alkyl, for example 2-dimethylaminoethyl, 2-diethylaminoethyl or 3-dimethylaminopropyl, or etherified hydroxy-lower alkyl, wherein the etherified hydroxyl group, especially lower alkoxy, is separated from the oxygen atom by at least two carbon atoms, such as 2- or 3-lower alkoxy-lower alkyl, for example 2-methoxyethyl or 2-ethoxyethyl. An optionally substituted araliphatic hydrocarbon radical $R_3$ is above all an optionally substituted phenyl-lower alkyl radical, especially 1-phenyl-lower alkyl radical with 1-3 optionally substituted phenyl radicals, such as benzyl or diphenylmethyl, possible substituents being, for example, esterified or etherified hydroxy, such as halogen, for example fluorine, chlorine or bromine, or lower alkoxy, such as methoxy.

The acyl radical $R_3$ of an aliphatic carboxylic acid is above all optionally substituted lower alkanoyl, for example acetyl, propionyl or pivaloyl, and such radicals can be substituted, for example by esterified or etherified hydroxyl, such as halogen, for example fluorine or chlorine, or lower alkoxy, for example methoxy or ethoxy. The acyl radical $R_3$ of an aromatic carboxylic acid is, for example, optionally substituted benzoyl, such as benzoyl or benzoyl substituted by esterified or etherified hydroxyl, for example halogen, such as fluorine or chlorine, or lower alkoxy, such as methoxy or ethoxy, or lower alkyl, for example methyl.

The compounds of the formula II, as well as their 1-oxides and salts, possess valuable pharmacological properties or can be used as intermediate products for the manufacture of such compounds. Compounds of the formula II wherein, for example, $R_1^a$ represents an acyl radical Ac occurring in pharmacologically active N-acyl derivatives of 6β-amino-penam-3-carboxylic acid compounds or 7β-amino-3-cephem-4-carboxylic acid compounds and $R_1^b$ represents hydrogen, or wherein $R_1^a$ and $R_1^b$ together represent a 1-oxo-3-aza-1,4-butylene radical which is preferably substituted in the 2-position, for example by an aromatic or heterocyclic radical, and preferably substituted in the 4-position, for example by 2 lower alkyl, such as methyl, $R_2$ denotes hydroxyl or an etherified hydroxyl group $R_2^A$ which, together with the carbonyl group, forms an esterified carboxyl group which can easily be split under physiological conditions, and $R_3$ has the abovementioned meaning, and in which the double bond is preferably in the 3,4-position of the cephem ring, or salts of such compounds having salt-forming groups are effective against micro-organisms such as Gram-positive bacteria, for example *Staphylococcus aureus*, (for example in mice at doses of about 0.001 to about 0.02 g/kg p.o.), and Gram-negative bacteria, for example, *Escherichia coli*, (for example in mice in doses of about 0.001 to about 0.05 g/kg p.c.) and also *Klebsiella pneumoniae*, *Proteus vulgaris* or *Salmonella typhosa*, and especially also against penicillin-resistant bacteria. These new compounds can therefore be used accordingly, for example in the form of antibiotically active preparations.

Compounds of the formula II, wherein the double bond of the cephem ring assumes the 2,3-position, or 1-oxides of compounds of the formula II, wherein the double bond is in the 3,4-position, and wherein $R_1^a$, $R_1^b$, $R_2$ and $R_3$ have the meanings indicated in the context of the formula I, or wherein the double bond of the cephem ring assumes the 3,4-position, $R_3$ has the meaning given above, the radicals $R_1^a$ and $R_1^b$ represent hydrogen, or $R_1^a$ denotes an amino protective group different from the above mentioned acyl radical and $R_1^b$ denotes hydrogen, or $R_1^a$ and $R_1^b$ together represent a bivalent amino protective group different from the abovementioned bivalent radicals, and $R_2$ represents hydroxyl, or $R_1^a$ and $R_1^b$ have the abovementioned meanings, $R_2$ represents a radical $R_2^A$ which together with the —C(=O)— grouping forms a protected carboxyl group which can preferably be split easily, and $R_3$ has the abovementioned meanings, are valuable intermediate products which can be converted in a simple manner, for example as is described below, into the abovementioned pharmacologically active compounds.

Compounds of particular value are those of the formula I and their 1-oxides, wherein $R_1^a$ denotes hydrogen or preferably an acyl radical contained in a fermentatively obtainable (that is to say naturally occurring) or biosynthetically, semi-synthetically or total-synthetically obtainable, in particular pharmacologically active, such as highly active, N-acyl derivative of a 6β-amino-penam-3-carboxylic acid compound or 7β-amino-3-cephem-4-carboxylic acid compound, or denotes an easily removable acyl radical of a carbonic acid half-derivative, in particular of a carbonic acid half-ester, and $R_1^b$ represents hydrogen, or wherein $R_1^a$ and $R_1^b$ together represent a 1-oxo-3-aza-1,4-butylene radical which is preferably substituted in the 2-position, for example by an aromatic or heterocyclic radical, and preferably substituted in the 4-position, for example by 2 lower alkyl, such as methyl, and $R_2$ represents hydroxyl, lower alkoxy which is optionally substituted, for example by optionally substituted aryloxy, such as lower alkoxyphenyloxy, for example 4-methoxyphenyloxy, lower alkanoyloxy, for example acetoxy or pivaloyloxy or arylcarbonyl, for example benzoyl, or halogen, for example chlorine, bromine or iodine, or optionally substituted aryl, such as phenyl, lower alkoxyphenyl, nitrophenyl or diphenyl, such as lower alkoxy, for example methoxy, ethoxy, n-propoxy, isopropoxy, n-butoxy, tert.-butoxy or tert.-pentoxy, bis-phenyloxymethoxy which is optionally substituted by lower alkoxy, for example bis-4-methoxyphenyloxy-methoxy, phenacyloxy, lower alkanoyloxy-methoxy, for example acetoxymethoxy or pivaloyloxymethoxy, 2-halogenolower alkoxy, for example 2,2,2-trichloroethoxy, 2-chloroethoxy, 2-bromoethoxy or 2-iodoethoxy, optionally substituted phenyl-lower alkoxy, especially 1-phenyllower alkoxy, such as phenylmethoxy, with such radicals being able to contain 1-3 phenyl radicals which are optionally substituted, for example by lower alkoxy, such as methoxy, nitro or phenyl, for example benzyloxy, 4-methoxy-benzyloxy, 2-biphenylyl-2-propoxy, 4-nitro-benzyloxy, diphenylmethoxy, 4,4'-dimethoxydiphenylmethoxy or trityloxy or represents acyloxy, such as lower alkoxycarbonyloxy, for example methoxycarbonyloxy or ethoxycarbonyloxy, or lower alkanoyloxy, for example acetoxy or pivaloyloxy, trilower alkylsilyloxy, for example trimethylsilyloxy, or amino or hydrazino which is optionally substituted, for example, by lower alkyl, such as methyl, or hydroxyl, for example amino, lower alkylamino or di-lower alkylamino, such as methylamino or dimethylamino, hydrazino, 2-lower alkylhydrazino or 2,2-di-lower alkylhydrazino, for example 2-methylhydrazino or 2,2-dimethylhydrazino, or hydroxy amino, and salts of such compounds with salt-forming groups.

Above all, in a compound of the formula I, or in a 1-oxide thereof, or in a salt of such a compound having salt-forming groups, $R_1^a$ represents hydrogen or an acyl radical contained in fermentatively obtainable (that is to say naturally occurring) or biosynthetically obtainable N-acyl derivatives of 6β-amino-penam-3-carboxylic acid compounds or 7β-amino-3-cephem-4-carboxylic acid compounds, such as a phenylacetyl or phenyloxyacetyl radical which is optionally substituted, for example by hydroxyl, also a lower alkanoyl or lower alkenoyl radical which is optionally substituted, for example by lower alkylthio, or lower alkenylthio, as well as by optionally substituted, such as acylated, amino and/or functionally modified, such as esterified, carboxyl, for example 4-hydroxy-phenylacetyl, hexanoyl, octanoyl or n-butylthioacetyl, and especially 5-amino-5-carboxy-valeryl, wherein the amino and/or the carboxyl groups are optionally protected and are present, for example, as acylamino or esterified carboxyl, phenylacetyl or phenyloxyacetyl, or an acyl radical occurring in highly active N-acyl derivatives of 6β-amino-penam-3-carboxylic acid compounds or 7β-amino-3-cephem-4-carboxylic acid compounds, such as formyl, halogenoethylcarbamoyl, for example 2-chloroethylcarbamoyl, cyanoacetyl, phenylacetyl, thienylacetyl, for example 2-thienylacetyl, or tetrazolylacetyl, for example 1-tetrazolylacetyl, especially phenylglycyl, wherein phenyl represents phenyl which is optionally substituted, or example by optionally protected hydroxyl, such as acyloxy, for example optionally halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxyphenyl (optionally with a protected hydroxyl group, such as an acylated hydroxyl group), and wherein the amino group is optionally substituted and represents, for example, sulphoamino group optionally present in the form of a salt, or an amino group which contains, as substituents, a hydrolytically removable trityl group or an optionally substituted carbamoyl group, such as an optionally substituted ureidocarbonyl group, for example ureidocarbonyl or N'-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as one of the abovementioned, for example optionally halogen-substituted or benzoyl-substituted, lower alkoxycarbonyl radicals, for example 2,2,2-trichloroethoxycarbonyl, 2-chloroethoxycarbonyl, 2-bromoethoxycarbonyl, 2-iodoethoxycarbonyl, tert.-butoxycarbonyl or phenacyloxycarbonyl, or a suitable acyl radical of a carbonic acid half-amide, such as carbamoyl or N-methylcarbamoyl, and also α-thienyl-glycyl, such as α-2-α-3-thienylglycyl, α-furylglycyl, such as α-2-furylglycyl, α-isothiazolylglycyl, such as α-4-isothiazolyl-glycyl, 1-amino-cyclohexylcarbonyl or aminopyridinium, for example 4-aminopuridinium (optionally with a substituted amino group, for example as indicated above), also α-carboxy-phenylacetyl or α-carboxy-2-thienylacetyl (optionally with a functionally modified carboxyl group, for example a carboxyl group present in the form of a salt, such as a sodium salt, or in the form of an ester, such as a lower alkyl ester, for example methyl or ethyl ester, or phenyl-lower alkyl ester, for example diphenylmethyl ester), α-sulphophenylacetyl (optionally with a sulpho group which is functionally modified, for example like the carboxyl group), α-phosphono-, α-O-methyl-phosphono- or α-O,O-dimethyl-phosphonophenylacetyl, or α-hydroxyphenylacetyl (optionally with a functionally modified hydroxyl group, especially with an acyloxy group, wherein acyl denotes an acyl radical hich can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as one of the abovementioned lower alkoxycarbonyl radicals which are, for example, optionally substituted by halogen or benzoyl, for example 2,2,2-trichloroethoxycarbonyl, 2-chloroethoxycarbonyl, 2-bromoethoxycarbonyl, 2-iodoethoxycarbonyl, tert.-butoxycarbonyl or phenacyloxycarbonyl, and also formyl), or pyridylthioacetyl, for example 4-pyridylthioacetyl, for example represents an acyl radical of the formula A, and $R_1^b$ represents hydrogen, or $R_1^a$ and $R_1^b$ together represent a 1-oxo-3-aza-1,4-butylene radical which is preferably substituted in the 2-posiiton by phenyl which is optionally substituted by protected hydroxyl, such as acyloxy, for example optionally halogen-substituted lower alkoxycarbonyloxy or lower alkanoyloxy, and/or by halogen, for example chlorine, for example phenyl or 3- or 4-hydroxyphenyl, 3-chloro-4-hydroxyphenyl or 3,5-dichloro-4-hydroxy-phenyl (optionally with a hydroxyl group which is protected, for example, acylated), and which optionally contains 2 lower alkyl, such as methyl, in the 4-position, and $R_2$ represents hydroxyl, lower alkoxy, especially α-poly-branched lower alkoxy, for example tert.-butoxy, also methoxy or ethoxy, 2-halogeno-lower alkoxy, for example 2,2,2-trichloroethoxy, 2-iodoethoxy or 2-chloroethoxy or 2-bromoethoxy which can easily be converted into 2-iodoethoxy, phenacyloxy, 1-phenyl-lower alkoxy with 1–3 phenyl radicals which are optionally substituted by lower alkoxy or nitro, for example 4-methoxybenzyloxy, 4-nitrobenzyloxy, diphenylmethoxy, 4,4'-dimethoxydiphenylmethoxy or trityloxy, lower alkanoyloxymethoxy, for example acetoxymethoxy or pivaloyloxymethoxy, lower alkoxycarbonyloxy, for example ethoxycarbonyloxy, or lower alkanoyloxy, for example acetoxy.

The invention above all relates in particular to compounds of the formula I, and 1-oxides thereof, wherein $R_1^b$ denotes hydrogen, $R_1^a$ denotes hydrogen, cyanoacetyl or an acyl group of the formula

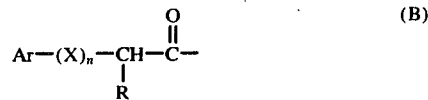

wherein Ar represents phenyl and also hydroxyphenyl, for example 3-or 4-hydroxyphenyl, or hydroxychlorophenyl, for example 3-chloro-4-hydroxyphenyl or 3,5-dichloro-4-hydroxy-phenyl, it being possible for hydroxy substituents in such radicals to be protected by acyl radicals, such as optionally halogenated lower alkoxycarbonyl radicals, for example tert.-butoxycarbonyl or 2,2,2-trichloroethoxycarbonyl, as well as thienyl, for example 2- or 3-thienyl, and also pyridyl, for example 4-pyridyl, aminopyridinium, for example 4-aminopyridinium, furyl, for example 2-furyl, isothiazolyl, for example 4-isothiazolyl, or tetrazolyl, for example 1-tetrazolyl, X represents oxygen or sulphur, n represents 0 or 1 and R represents hydrogen, or, if n represents O, R represents optionally protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or 3-guanylureido, also sulphoamino or tritylamino, optionally protected carboxyl, for example esterified carboxyl, such as phenyllower alkoxycarbonyl, for example diphenylmethoxycarbonyl, optionally protected sulpho, such as sulpho present in the form of an alkali metal salt, such as a sodium salt, optionally protected hydroxyl, such as acyloxy, for example α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, also formyloxy, or O-lower alkylphosphono or O,O-di-lower alkylphosphono, for example O-methyl-phosphono or O,O-dimethylphosphono, or denotes a 5-amino-5-carboxy-valeryl radical, wherein the amino and/or carboxyl groups are optionally protected and are, for example, present as acylamino, for example lower alkanoylamino, such as acetylamino, halogeno-lower alkanoylamino such as dichloroacetylamino, or phthaloylamino, or as esterified carboxyl, such as phenyl-lower alkoxycarbonyl, for example diphenylmethoxycarbonyl, $R_2$ represents hydroxyl and lower alkoxy, especially α-poly-branched lower alkoxy, for example tert.-butoxy, 2-halogenolower alkoxy, for example 2,2,2-trichloroethoxy, 2-iodoethoxy or 2-bromoethoxy, or diphenylmethoxy which is optionally substituted, for example by lower alkoxy, for example methoxy, for example diphenylmethoxy or 4,4'-dimethoxydiphenylmethoxy and salts, of such compounds having salt-forming groups.

In compounds of the formula I or 1-oxides thereof, which should be designated as being particularly valuable, $R_1^a$ represents hydrogen or the acyl radical of the formula B, wherein Ar denotes phenyl, X denotes oxygen, n denotes O or 1 and R denotes hydrogen, or, if n represents O, denotes optionally protected amino, such as acylamino, for example α-poly-branched lower alkoxycarbonylamino, such as tert.-butoxycarbonylamino, or 2-halogeno-lower alkoxycarbonylamino, for example 2,2,2-trichloroethoxycarbonylamino, 2-iodoethoxycarbonylamino or 2-bromoethoxycarbonylamino, or optionally protected hydroxyl, such as acyloxy, for example α-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, and also formyloxy, or denotes O-lower alkylphosphono or O,O-di-lower alkylphosphono, for example O-methylphosphono or O,O-dimethylphosphono, or represents a 5-amino-5-carboxy-valeryl radical, wherein the amino and carboxyl group are optionally protected and, for example, are in the form of acylamino, for example lower alkanoylamino, such as acetylamino, halogeno-lower alkanoylamino, such as dichloroacetylamino, or phthaloylamino, or of esterified carboxyl, such as phenyl-lower alkoxycarbonyl, for example diphenylmethoxycarbonyl, $R_1^b$ represents hydrogen and $R_2$ denotes hydroxyl and also lower alkoxy which is optionally halogen-substituted, for example chlorine-substituted, bromine-substituted or iodine-substituted, in the 2-position, especially α-poly-branched lower alkoxy, for example tert.-butoxy, or 2-halogeno-lower alkoxy, for example 2,2,2-trichloroethoxy, 2-iodoethoxy or 2-bromoethoxy, or optionally lower alkoxy-substituted, such as methoxy-substituted, diphenylmethoxy, for example diphenylmethoxy or 4,4'-dimethoxy-diphenylmethoxy.

Particularly valuable individual compounds which can be manufactured according to the invention are 3-methylene-7β-(D-α-tert.-butoxycarbonylamino-phenylacetylamino)-cepham-4α-carboxylic acid, 3-methylene-7β-(phenylacetylamino)-cepham-4α-carboxylic acid, 7η-amino-3-methylene-cepham-4α-carboxylic acid, 3-methylene-7β-(5-benzoylamino-adipoylamino)-cepham-4α-carboxylic acid, 3-methylene-7β-(D-α-p-methoxybenzyloxycarbonylamino-α-phenylacetylamino)-cepham-4α-carboxylic acid, 3-methylene-7β-(D-α-tert.-butoxycarbonylamino-phenylacetylamino)-cepham-4α-carboxylic acid 1-oxide, 3-methylene-7β-(D-α-tert.-butoxycarbonylamino-phenylacetylamino)-cepham-4α-carboxylic acid and 3-methylene-7β-phenoxyacetylamino-cepham-4α-carboxylic acid as well as their salts and esters, for example the diphenylmethyl esters.

The new process, according to the invention, for the manufacture of 7β-amino-3-methylene-cepham-4-carboxylic acid compounds of the formula I and of their salts is characterised in that a 7β-amino-3-acetoxymethyl-3-cephem-4-carboxylic acid compound of the formula

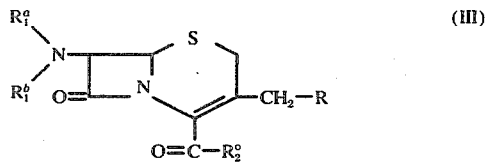

(III)

wherein $R_1^a$ and $R_1^b$ have the abovementioned meaning, R denotes an acyloxy group, $R_2^o$ has the meaning of $R_2$ or R and $R_2^o$ together denote an epoxy group, or a 1-oxide thereof, or a salt of such a compound, is reduced with a metal which has a normal potential of −2.4 to −0.40 volt, or an amalgam thereof, at a pH of 1 to 8, in the presence of water and, if desired, a resulting compound of the formula I or a resulting 1-oxide thereof is converted into a compound of the formula I and/or, if desired, a resulting compound having a salt-forming group is converted into a salt or a resulting salt is converted into the free compound or into another salt and/or, if desired, a resulting isomer mixture is separated into the individual isomers.

Examples of metals with a normal potential of −2.4 to −0.40 volt which should be mentioned are magnesium, manganese, zinc, iron, chromium, cadmium and especially aluminium. They are used in a coarse granular form or especially in a fine granular form. The metals are preferably employed as amalgams or in a superficially amalgamated form. Processes for the manufacture of such amalgamated metals are known. A preferred reducing agent is amalgamated aluminium which is obtained by treatment of aluminium grit with a soluble mercury-II salt, for example with 0.5 percent strength mercury-(II) chloride or mercury-II acetate solution.

The reaction according to the invention is carried out in a pH range of 1 to 8, preferably 2 to 7. Optimum results are obtained in a range of pH 6 to 7. The pH value can be adjusted to the desired value by organic or inorganic acids and can be kept constant by continuous addition of further quantities of acid during the reaction. Suitable organic acids are in particular water-soluble acids or acids which are soluble in the solvent mixture used, such as lower aliphatic carboxylic acids, for example lower alkanecarboxylic acids, such as formic acid, acetic acid, propionic acid, butyric acid or valeric acid, or lower aliphatic sulphonic acids, such as methanesulphonic acid, ethanesulphonic acid or propanesulphonic acid, aromatic carboxylic acids, such as benzoic acid, aromatic sulphonic acids, such as benzenesulphonic acid, aliphatic polycarboxylic acids, such as dicarboxylic acids, such as lower alkanedicarboxylic acids or alkenedicarboxylic acids, for example oxalic acid, maleic acid, malonic acid or succinic acid, aromatic polycarboxylic acids, such as trimellitic acids or trimesic acid, or corresponding polysulphonic acids, such as o-benzenedisulphonic acid and the like. The acids mentioned can carry substituents, amongst which there should in particular be mentioned halogen, such as fluorine or chlorine, or lower alkyl, lower alkoxy, hydroxyl or amino groups. Examples of such acids are chloroacetic acid, trifluoroacetic acid, p-toluenesulphonic acid, p-methoxyphenylacetic acid, tartronic acid, tartaric acid, citric acid and the known aminoacids of which the amino groups can optionally be substituted, for example ethylenediaminetetraacetic acid.

Inorganic acids which can be used for the reaction are above all mineral acids, such as hydrogen halide acids, for example hydrofluoric acid or hydrochloric acid, halogen-oxygen acids, such as perchloric acid, acids derived from sulphur, such as hydrogen sulphide and sulphuric acid, and acids derived from phosphorus, such as phosphoric acid or metaphosphoric acid.

Some of these acids not only serve to adjust the pH value but also, as is explained in more detail below, to form a complex with the metal cations formed during the reaction, or to precipitate them from the solution.

Amongst the acids mentioned, for example, hydrogen fluoride can form soluble complexes with aluminium$^{3+}$ cations, oxalic acid with aluminium$^{3+}$, zinc$^{2+}$ and chromium$^{3+}$ cations, tartaric acid with magnesium$^{2+}$ cations, citric acid with chromium$^{3+}$ cations, metaphosphoric acid with magnesium$^{2+}$ cations and etylenediaminetetraacetic acid with aluminium$^{3+}$, magnesium$^{2+}$, manganese$^{2+}$, zinc$^{2+}$, chromium$^{3+}$, iron$^{2+}$ and cadmium$^{2+}$ cations, as a result of favourable complex formation constants.

Hydrogen sulphide can, for example, precipitate manganese$^{2+}$, zinc$^{2+}$, iron$^{2+}$ and cadmium$^{2+}$ ions from aqueous solutions and phosphoric acid can precipitate magnesium$^{2+}$ and iron$^{2+}$ ions from aqueous solutions.

The reaction according to the invention is optionally carried out in the presence of reagents which increase the reducing capacity of the metals or amalgams. These include, in particular, reagents which remove the metal cations formed in the reaction from the redox equilibrium. Such reagents are, in particular, chemical compounds which either bind the metal cations in a complex form or precipitate them from the reaction solution. Suitable complex-forming agents are the anions of the complex-forming acids which have already been mentioned. Accordingly, it is also possible to employ, instead of these acids, their soluble salts, the cations of the salts having to be different than those produced in the reaction. Accordingly, preferred salts are especially corresponding alkali metal salts, such as lithium, sodium or potassium salts or also ammonium or substituted ammonium salts, such as mono-, di- or tetra-lower alkylammonium, for example -methylammonium, -ethylammonium or -propylammonium, salts, and the like. Of course the desired pH must be obtained by addition of another acid if such salts are used.

The reaction according to the invention is carried out in water, optionally with the addition of one or more organic solvents. As such it is in particular possible to use organic solvents which are inert under the reaction conditions, such as lower aliphatic or aromatic, optionally N-monosubstituted or N,N-disubstituted, for example lower alkyl-substituted, amides, for example diethylformamide or preferably dimethylformamide, lower dialkylsulphoxides, for example dimethylsulphoxide, lower alkanols, for example methanol or ethanol, water-soluble ethers, such as cyclic ethers, for example tetrahydrofurane or dioxane, lower ketones, for example acetone, or lower nitriles, for example acetonitrile. If a solvent or solvent mixture is used, it contains at least 10 to 20% of water.

To prevent foaming, anti-foaming agents can be added to the reaction mixture. For example, lower carboxylic acid esters, for example ethyl acetate, can prevent foaming.

The reaction temperature and reaction time depend essentially on the nature of the starting material of the formula III which is employed, the nature of the metal or metal amalgam employed, the nature of the solvent and the pH value. The temperature can be between about 0° and 100° and is preferably between about 25° and 50°. The reaction time varies, from a few minutes to a few hours. In general, the reaction is complete after about ½ to 1 hour.

Under the conditions mentioned, especially the optimum conditions, practically no isomerisation products, and in particular no 3-methyl-3-cephem compounds, are obtained.

Starting materials of the formula III and 1-oxides thereof are known or can be manufactured according to known methods.

In a starting material of the formula III or a 1-oxide thereof, R as an acyloxy group is a lower alkanoyloxy group with 1 to 7, preferably 1 to 4, carbon atoms, such as formyloxy, propionyloxy, butyryloxy, valeryloxy, isovaleryloxy, pivalyloxy and especially acetoxy.

Preferably, in a starting material of the formula II or a 1-oxide thereof, the radical $R_1{}^a$ denotes hydrogen or an amino protective group $R_1{}^A$, such as an acyl group Ac, wherein free functional groups which may be present, for example amino, hydroxyl, carboxyl or phosphono groups, can be protected in a manner which is in itself known, amino groups, for example, by acylation, tritylation, silylation or stannylation and hydroxyl, carboxyl or phosphono groups, for example, by etherification or esterification, including silylation and stannylation, $R_1{}^b$ denotes hydrogen, R denotes the acetoxy group and $R_2{}^o$ in particular denotes hydroxyl and also an etherified hydroxyl group $R_2{}^A$ which together with the —C(=O)— grouping forms an esterified carboxyl group which can be split, especially under mild conditions, it being possible for functional groups which may be present in a carboxyl protective group $R_2{}^A$ to be protected in a manner which is in itself known, for example as indicated above, or R and $R_2{}^o$ together denote an epoxy group. A group $R_2{}^A$ is, for example, in particular an optionally halogen-substituted lower alkoxy group, such as α-poly-branched lower alkoxy, for example tert.-butoxy, or 2-halogeno-lower alkoxy, wherein halogen represents, for example, chlorine, bromine or iodine, above all, 2,2,2-trichloroethoxy, 2-bromoethoxy, or 2-iodoethoxy, or an optionally substituted 1-phenyl-lower alkoxy group, such as a 1-phenyl-lower alkoxy group containing lower alkoxy, for example methoxy, or containing nitro, such as benzyloxy or diphenylmethoxy which are optionally substituted, for example as indicated, for example benzyl, 4-methoxybenzyl, 4-nitrobenzyl, diphenylmethoxy or 4,4'-dimethoxy-diphenylmethoxy, and also an organic silyloxy or stannyloxy group, such as tri-lower alkyl-silyloxy, for example trimethylsilyloxy.

Preferred starting materials of the formula III are those which lead to the particularly valuable end products of the formula I, for example those wherein $R_1{}^a$ denotes hydrogen or an acyl group Ac which represents an acyl radical of an organic carboxylic acid, preferably with up to 18 carbon atoms, contained in a naturally occurring or a biosynthetically semi-synthetically or fully synthetically obtainable, preferably pharmacologically active N-acyl derivative of a 6-aminopenam-3-carboxylic acid compound or 7-amino-3-cephem-4-carboxylic acid compound, or an easily removable acyl radical, especially of a carbonic acid half-derivative, $R_1{}^b$ denotes hydrogen, R represents the acetoxy group and $R_2{}^o$ represents a hydroxyl group or wherein R and $R_2{}^o$ together represents an epoxy group, 1-oxides thereof or the salts of such a compound.

Example of starting materials of the formula III are 7β-(D-α-tert.-butoxycarbonylamino-α-phenylacetylamino)-cephalosporanic acid, 7β-(α-phenylacetylamino)-cephalosporanic acid, 7β-aminocephalosporanic acid, N-benzoyl-cephalosporin C, N-benzoyl-desacetyl-cephalosporin C-lactone, 7β-(D-α-p-methoxybenzoxycarbonylamino-α-phenylacetamino)-cephalosporanic acid, 7α-(D-α-tert.-butoxycarbonylaminophenylacetylamino)-cephalosporanic acid 1-oxide, 7β-phenoxyacetylamino-cephalosporanic acid and the salts of the acids mentioned.

Preferred salts of the starting materials of the formula III, wherein $R_2{}^o$ is hydroxyl, or of the 1-oxides thereof, are the metal salts, such as alkali metal salts, especially the sodium salts or potassium salts, and also the ammonium salts of ammonia or suitable organic amines, especially of lower alkylamines, such as triethylamine, and of hydroxy-lower alkylamines, such as 2-hydroxyethylamine, or the inner salts.

Starting materials of the formula III, 1-oxides thereof or their salts, can be employed as crude products or, preferably, in the pure form. They can be purified according to customary methods, for example by chromatography or via suitable derivatives. For example, a starting material of the formula II, wherein $R_2^0$ is hydroxyl, or a 1-oxide thereof, can be purified by converting it into one of the abovementioned salts, for example the sodium salt or 2-hydroxyethylamine salt, from which it can then be recovered in a pure form or be converted into another salt.

In the process according to the invention, and in additional measures which may have to be carried out it is possible, where necessary, temporarily to protect, in a manner which is in itself known, free functional groups, which do not participate in the reaction, in the starting substances or in compounds obtainable according to the process, for example to protect free amino groups by, for example, acylation, tritylation or silylation free hydroxy or mercapto groups by, for example, etherification or esterification and free carboxyl groups by, for example, esterification, including silylation, and in each case to liberate such groups, if desired in a manner which is in itself known after the reaction has been carried out.

In a compound of the formula I obtainable according to the invention or a 1-oxide thereof, and possessing a protected, especially esterified, carboxyl group of the formula $-C(=O)-R_2^A$, the latter can be converted into the free carboxyl group in a manner which is in itself known, for example depending on the nature of the group $R_2^A$. An esterified carboxyl group, for example a carboxyl group esterified by a lower alkyl radical, especially methyl or ethyl, can be converted into a free carboxyl group by hydrolysis in a weakly basic medium, for example by treatment with an aqueous solution of an alkali metal hydroxide or carbonate or alkaline earth metal hydroxide or carbonate, for example sodium hydroxide or potassium hydroxide, preferably at a pH value of about 9 to 10, and optionally in the presence of a lower alkanol. A carboxyl group esterified by a suitable 2-halogeno-lower alkyl group or by an arylcarbonylmethyl group can be split, for example, by treatment with a chemical reducing agent, such as a metal, for example zinc, or a reducing metal salt, such as a chromium-II salt, for example chromium-II chloride, usually in the presence of a hydrogen donor which is capable of producing nascent hydrogen together with the metal, such as an acid, above all acetic acid and also formic acid, or an alcohol, water being added preferably, a carboxyl group esterified by an arylcarbonylmethyl group can also be split by treatment with a nucleophilic, preferably salt-forming, reagent, such as sodium thiophenolate or sodium iodide, a carboxyl group esterified by a suitable arylmethyl grouping can be split, for example, by irradiation, preferably with ultraviolet light, for example below 290 m$\mu$, if the arylmethyl group represents, for example, a benzyl radical which is optionally substituted in the 3-, 4- and/or 5-position, for example by lower alkoxy and/or nitro groups, or with ultraviolet light of longer wavelengths, for example above 290 m$\mu$, if the arylmethyl group denotes, for example, a benzyl radical which is substituted by a nitro group in the 2-position, a carboxyl group which is esterified by a suitably substituted methyl group, such as tert.-butyl or diphenylmethyl can be split, for example, by treatment with a suitable acid agent, such as formic acid or trifluoroacetic acid, optionally with the addition of a nucleophilic compound, such as phenol or anisole, an activated esterified carboxyl group can be split by hydrolysis, for example by treatment with an acid or weakly basic aqueous agent, such as hydrochloric acid or aqueous sodium bicarbonate or an aqueous potassium phosphate buffer of pH about 7 to about 9, and an esterified carboxyl group which can be split hydrogenolytically can be split by hydrogenolysis, for example by treatment with hydrogen in the presence of a noble metal catalyst, for example a palladium catalyst.

A carboxyl group protected, for example, by silylation or stannylation can be liberated in the usual manner, for example by treatment with water or an alcohol.

Resulting compounds of the formula I, or 1-oxides thereof, can be converted in a manner which is in itself known into other compounds of the formula I.

In a resulting compound it is possible, for example, to split off an amino protective group $R_1^A$ or $R_1^b$, especially an easily removable acyl group, in a manner which is in itself known, for example an $\alpha$-polybranched lower alkoxycarbonyl group or phenyl-lower alkoxycarbonyl group, such as tert.-butoxycarbonyl or p-methoxyphenylmethoxycarbonyl, by treatment with trifluoroacetic acid, and a 2-halogeno-lower alkoxycarbonyl group, such as 2,2,2-trichloroethoxycarbonyl or 2-iodoethoxycarbonyl or a phenacyloxycarbonyl group, by treatment with a suitable reducing metal or corresponding metal compound, for example zinc, or a chromium-II compound, such as chromium-II chloride or chromium-II acetate, advantageously in the presence of an agent which together with the metal or the metal compound generates nascent hydrogen, preferably in the presence of aqueous acetic acid. It is furthermore possible, in a resulting compound of the formula I, wherein a carboxyl group of the formula $-C(=O)-R_2$ preferably represents a carboxyl group which is protected, for example by esterification, including by silylation, for example by reaction with a suitable organic halogenosilicon compound or halogen-tin-IV compound, such as trimethyl chlorosilane or tri-n-butyl-tin chloride, to split off an acyl group $R_1^A$ or $R_1^b$, wherein optionally present free functional groups are optionally protected, by treatment with an imide-halide-forming agent, reaction of the resulting imide-halide with an alcohol and splitting of the imino-ether formed, it being possible for a protected carboxyl group, for example a carboxyl group protected by an organic silyl radical, already to be liberated in the course of the reaction.

Imide-halide-forming agents in which halogen is bonded to an electrophilic central atom are above all acid halides, such as acid bromides and especially acid chlorides. The acid halides are above all acid halides of inorganic acids, above all of acids containing phosphorus, such as phosphorus oxyhalides, phosphorus trihalides and especially phosphorus pentahalides, for example phosphorus oxychloride, phosphorus trichloride and above all phosphorus pentachloride, and also pyrocatechyl-phosphorus trichloride, as well as acid halides, especially acid chlorides, of acids containing sulphur or of carboxylic acids, such as thionyl chloride, phosgene or oxalyl chloride.

The reaction with one of the imide-halide-forming agents mentioned is usually carried out in the presence of a suitable base, especially of an organic base, above all of a tertiary amine, for example a tertiary aliphatic monoamine or diamine, such as a tri-lower alkylamine, for example trimethylamine, triethylamine or ethyldiisopropylamine, also a N,N,N',N'-tetra-lower alkyl-lower alkylenediamine, for example N,N,N',N'-tetramethyl-1,5-pentylenediamine or N,N,N',N'-tetramethyl-1,6-hexylenediamine, a monocyclic or bicyclic monoamine or diamine, such as a N-substituted, for example N-lower alkylated, alkyleneamine, azaalkyleneamine or oxaalkyleneamine, for example N-methyl-piperidine or N-methyl-morpholine, as well as 2,3,4,6,7,8-hexahydro-pyrrolo[1,2-a]pyrimidine (diazabicyclononene; DBN), or a tertiary aromatic amine such as a di-lower alkylaniline, for example N,N-dimethylaniline, or above all a tertiary heterocyclic, monocyclic or bicyclic, base, such as quinoline or isoquinoline, especially pyridine, preferably in the presence of a solvent, such as an optionally halogenated, for example chlorinated, aliphatic or aromatic hydrocarbon, for example methylene chloride. It is possible to use approximately equimolar amounts of the imide-halide-forming agent and of the base; the latter can however also be present in more than or less than equimolar amount, for example in about 0.2-fold to about 1-fold amount or in, say, up to 10-fold, in particular about 3-fold to 5-fold, excess.

The reaction with the imide-halide-forming agent is preferably carried out with cooling, for example at temperatures of about $-50°$ C to about $+10°$ C, but it is also possible to work at higher temperatures, that is to say, for example, up to about $75°$ C, if the stability of the starting substances and of the products permits a higher temperature.

The imide-halide product which is usually further processed without isolation, is reacted according to the process with an alcohol, preferably in the presence of one of the above-mentioned bases, to give the imino-ether. Examples of suitable alcohols are aliphatic as well as araliphatic alcohols, above all optionally substituted, such as halogenated, for example chlorinated, lower alkanols or lower alkanols possessing additional hydroxyl groups, for example ethanol, propanol or butanol but especially methanol, also 2-halogeno-lower alkanols, for example 2,2,2-trichloroethanol or 2-bromoethanol, and optionally substituted phenyl-lower alkanols, such as benzyl alcohol. Usually an excess, for example up to about 100-fold excess, of the alcohol is employed and the reaction is preferably carried out with cooling, for example at temperatures of about $-50°$ C to about $10°$ C.

The imino-ether product can advantageously be split without isolation. The splitting of the imino-ether can be achieved by treatment with a suitable hydroxy compound, preferably by means of hydrolysis. Preferably, water or an aqueous mixture of an organic solvent, such as an alcohol, especially a lower alkanol, for example methanol, is used. The reaction is usually carried out in an acid medium, for example at a pH value of about 1 to about 5 which can, if necessary, be obtained by adding a basic agent, such as an aqueous alkali metal hydroxide, for example sodium hydroxide or potassium hydroxide, or an acid, for example a mineral acid, or an organic acid, such as hydrochloric acid, sulphuric acid, phosphoric acid, fluoboric acid, trifluoroacetic acid or p-toluenesulphonic acid.

The three-stage process for splitting off an acyl group, described above, is advantageously carried out without isolation of the imide-halide and imino-ether intermediate products, usually in the presence of an organic solvent which is inert towards the reactants, such as an optionally halogenated hydrocarbon, for example methylene chloride, and/or in an inert gas atmosphere, such as nitrogen atmosphere.

If the imide-halide intermediate product obtainable according to the above process, instead of being reacted with an alcohol, is reacted with a salt, such as an alkali metal salt, of a carboxylic acid, especially of a sterically hindered carboxylic acid, a compound of the formula I, wherein both radicals $R_1^a$ and $R_1^b$ represent acyl groups, is obtained.

In a compound of the formula I, wherein both radicals $R_1^a$ and $R_1^b$ represent acyl groups, one of these groups, preferably the sterically less hindered group, can be removed selectively, for example by hydrolysis or aminolysis.

In a compound of the formula I, or a 1-oxide thereof, wherein $R_1^A$ and $R_1^b$ together with the nitrogen atom represent a phthalimido group, the latter can be converted into the free amino group, for example by hydrazinolysis, that is to say on treatment of such a compound with hydrazine.

Certain acyl radicals $R_1^A$ of an acylamino grouping in compounds obtainable according to the invention such as, for example, the 5-amino-5-carboxy-valeryl radical, wherein carboxyl is optionally protected, for example by esterification, especially by diphenylmethyl, and/or the amino group is optionally protected, for example by acylation, especially by halogeno-lower alkanoyl, such as dichloroacetyl, can also be split off by treatment with a nitrosylating agent, such as nitrosyl chloride, with a carbocyclic arenediazonium salt, such as benzenediazonium chloride, or with an agent which releases positive halogen, such as a N-halogen-amide or -imide, for example N-bromosuccinimide, preferably in a suitable solvent or solvent mixture, such as formic acid, together with a nitro- or cyano-lower alkane, and treatment of the reaction product with a hydroxylic agent, such as water or a lower alkanol, for example methanol or, if in the 5-amino-5-carboxy-valeryl radical $R_1^A$ the amino group is unsubstituted and the carboxyl group is protected, for example by esterification, and $R_1^b$ preferably represents an acyl radical but can also denote hydrogen, by leaving the substance to stand in an inert solvent, such as dioxane or a halogenated aliphatic hydrocarbon, for example methylene chloride and, if necessary, working up the free or monoacylated amino compound according to methods which are in themselves known.

A formyl group $R_1^A$ can also be split off by treatment with an acid agent, for example p-toluenesulphonic acid or hydrochloric acid, a weakly basic agent, for example dilute ammonia, or a decarbonylating agent, for example tris-(triphenylphosphine)-rhodium chloride.

A triarylmethyl group, such as the trityl group $R_1^A$, can be split off, for example, by treatment with an acid agent, such as a mineral acid, for example hydrochloric acid.

In a compound of the formula I, or a 1-oxide thereof, wherein $R_1^a$ and $R_1^b$ represent hydrogen, the free amino group can be acylated according to methods of acylation which are in themselves known, for example by treatment with carboxylic acids or reactive acid derivatives thereof, such as halides, for example fluorides or chlorides, also pseudo-halides, such as cyanocarbonyl compounds corresponding to the acids, or anhydrides (by which there are also to be understood the inner anhydrides of carboxylic acids, that is to say ketenes, or of carbamic or thiocarbamic acids, that is to say isocyanates or isothiocyanates, or mixed anhydrides, such as those which can be formed for example, with halogenoformic acid lower alkyl esters, such as chloroformic acid ethyl esters or isobutyl esters, or with trichloroacetic acid chloride), or activated esters, or with substituted formimino derivatives, such as substituted N,N-dimethylchloroformimino derivatives, or a N-substituted N,N-diacylamine, such as a N,N-diacylate aniline, the reaction being carried out, if necessary, in the presence of suitable condensation agents, for example of carbodiimides, such as dicyclohexylcarbodiimide, when using acids, or, for example, of basic agents, such as triethylamine or pyridine, when using reactive acid derivatives, it also being possible, where appropriate, to start from salts, for example ammonium salts of compounds of the formula I, or a 1-oxide thereof, wherein $R_2$ represents a hydroxyl group.

An acyl group can also be introduced by acylating a compound of the formula I, wherein $R_1^a$ and $R_1^b$ together represent an ylidene radical (which can also be introduced subsequently, for example by treating a compound wherein $R_1^a$ and $R_1^b$ represent hydrogen, or a 1-oxide thereof, with an aldehyde, such as an aliphatic, aromatic or araliphatic aldehyde), for example according to the methods indicated above, and the acylation product can be hydrolysed, preferably in a neutral or weakly acid medium.

An acyl group can also be introduced stepwise. Thus, for example, it is possible to introduce into a compound of the formula I, or 1-oxide thereof, having a free amino group, a halogeno-lower alkanoyl group, for example bromoacetyl group, or, for example by treatment with a carbonic acid dihalide, such as phosgene, a halogenocarbonyl group, for example chlorocarbonyl group, and to react a N-(halogeno-lower alkanoyl)-amino compound or N-(halogenocarbonyl)-amino compound thus obtainable with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol and thus to obtain substituted N-lower alkanoylamino or N-hydroxycarbonylamino compounds. It is furthermore possible, for example, to react a compound of the formula I, or a 1-oxide thereof, wherein $R_1^a$ represents a glycyl group which is preferably substituted in the α-position, such as phenylglycyl, and $R_1^b$ represents hydrogen, with an aldehyde, for example formaldehyde, or a ketone, such as a lower alkanone, for example acetone, and thus to arrive at compounds of the formula I, or a 1-oxide thereof, wherein $R_1^A$ and $R_1^b$ together with the nitrogen atom represent a 5-oxo-1,3-diaza:cyclopentyl radical which is preferably substituted in the 4-position and is optionally substituted in the 2-position.

In both reactants, both rectants, free functional groups can temporarily be protected during the acylation reaction, in a manner which is in itself known and be liberated, after the acylation, by means of methods which are in themselves known. Thus it is preferentially possible to protect, for example, amino, hydroxyl, carboxyl or phosphono groups in the acyl radical during the acylation reaction, for example in the form of acylamino groups, such as those mentioned above, for example 2,2,2-trichloroethoxycarbonylamino, 2-bromoethoxycarbonylamino or tert.-butoxycarbonylamino groups, of acyloxy groups, such as those mentioned above, for example 2,2,2-trichloroethoxycarbonyloxy or 2-bromoethoxycarbonyl groups, of esterified carboxyl groups, such as those mentioned above, for example diphenylmethoxycarbonyl groups, or of O,O-disubstituted phosphono groups, such as those mentioned above, for example O,O-di-lower alkylphosphono, for example O,O-dimethyl-phosphono groups, and subsequently to split these protected groups, for example partially, optionally after conversion of the protective group, for example of a 2-bromoethoxycarbonyl group into a 2-iodoethoxycarbonyl group, for example split them by treatment with suitable reducing agents, such as zinc in the presence of aqueous acetic acid, or with trifluoroacetic acid, by hydrogenolysis or by treatment with an alkali metal halide.

The acylation can also be effected by replacement of an already existing acyl group by another, preferably sterically hindered, acyl group, for example according to the process described above, by manufacturing the imide-halide compound, treating this with a salt of an acid and splitting off hydrolytically one of the acyl groups present in the product thus obtainable, usually the sterically less hindered acyl group.

In a compound of the formula I, or a 1-oxide thereof, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as with a dihalogeno-di-lower alkylsilane or tri-lower alkyl-silyl halide, for example dichlorodimethylsilane or trimethylsilyl chloride, or by treatment with an optionally N-mono-lower alkylated, N,N-di-lower alkylated, N-trilower alkylsilylated or N-lower alkyl-N-trilower alkylsilylated N-(tri-lower alkylsilyl)-amine (see, for example, British Pat. No. 1,073,530), or by treatment with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or with a tri-lower alkyl-tin halide, for example tri-n-butyl-tin chloride (see, for example, Netherlands Published Specification No. 67/11,107).

In a compound of the formula I, or in a 1-oxide thereof, obtainable according to the process, which contains a free carboxyl group of the formula —C(=O)—$R_2$, such a group can be converted into a protected carboxyl group in a manner which is in itself known. Thus, an ester is obtained, for example, by treatment with a suitable diazo compound, such as a diazo-lower alkane, for example diazomethane or diazobutane, or a phenyl-diazo-lower alkane, for example diphenyldiazomethane, if necessary in the presence of a Lewis acid, for example boron trifluoride, or by reaction with an alcohol suitable for the esterification reaction, in the presence of an esterifying agent, such as a carbodiimide, for example dicyclohexylcarbodiimide, as well as carbonyldiimidazole, and also with a N,N′-disubstituted O- or S-substituted isourea or isothiourea, wherein a O-substituent and S-substituent are, for example, lower alkyl, especially tert.-butyl, phenyl-lower alkyl or cycloalkyl, and N-substituents or N'-substituents are, for example, lower alkyl, especially isopropyl, cycloalkyl or phenyl, or according to any other known and suitable esterification process, such as reaction of a salt of the acid with a reactive ester of an alcohol and of a strong inorganic acid, or a strong organic sulphonic acid. Furthermore, acid halides, such as acid chlorides (manufactured, for example, by treatment with oxalyl chloride), activated esters (formed, for example, with N-hydroxy-nitrogen compounds, such as N-hydroxy-succinimide), or mixed anhydrides (obtained, for example, with halogenoformic acid lower alkyl esters, such as chloroformic acid ethyl ester or chloroformic acid isobutyl ester, or with halogenoacetic acid halides, such as trichloroacetic acid chloride) can be converted into an esterified carboxyl group by reaction with alcohols, optionally in the presence of a base, such as pyridine.

In a resulting compound having an esterified grouping of the formula $-C(=O)-R_2$, this grouping can be converted into a different esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

Mixed anhydrides can be manufactured by reacting a compound of the formula I, having a free carboxyl group of the formula $-C(=O)-R_2$, or a 1-oxide thereof, preferably a salt, especially an alkali metal salt, for example a sodium salt, or ammonium salt, for example triethylammonium salt, thereof, with a reactive derivative, such as a halide, for example the chloride, of an acid, for example a halogenoformic acid lower alkyl ester or a lower alkanecarboxylic acid chloride.

In a compound obtainable according to the process, having a free carboxyl group of the formula $-C(=O)-R_2$, such a group can also be converted into an optionally substituted carbamoyl or hydrazinocarbonyl group, for which preferably reactive functionally modified derivatives, such as the above-mentioned acid halides, and generally esters, including also the above-mentioned activated esters, or mixed anhydrides of the appropriate acid are reacted with ammonia or amines, including hydroxylamine, or hydrazines.

A carboxyl group protected by an organic silyl or stannyl group can be formed in a manner which is in itself known, for example by treating compounds of the formula I, wherein $R_2$ represents hydroxyl, or salts thereof, such as alkali metal salts thereof, for example sodium salts thereof, with a suitable silylating or stannylating agent, such as one of the abovementioned silylating or stannylating agents; see, for example, British Pat. No. 1,073,530 or Netherlands Published Specification No. 67/17,107.

It is furthermore possible to liberate modified functional substituents in groups $R_1^A$, $R_1^b$ and/or $R_2$, such as substituted amino groups, acylated hydroxyl groups, esterified carboxyl groups or O,O'-disubstituted phosphono groups, according to methods which are in themselves known, for exaple those described above, or functionally to modify free functional substituents in groups $R_1^A$, $R_1^b$ and/or $R_2$, such as free amino, hydroxyl, carboxyl or phosphono groups, according to processes which are in themselves known, for example acylation or esterification or substitution. Thus, for example, an amino group can be converted into a sulphoamino group by treatment with sulphur trioxide, preferably in the form of a complex with an organic base, such as a tri-lower alkylamine, for example triethylamine, Furthermore, the reaction mixture obtained by reaction of an acid addition salt of a 4-guanylsemicarbazide with sodium nitrite can be reacted with a compound of the formula I, or a 1-oxide thereof, wherein, for example, the amino protective group $R_1^A$ represents an optionally substituted glycyl group, and the amino group can thus be converted into a 3-quanylureido group. Further, compounds with aliphatically bonded halogen, for example with an optionally substituted α-bromoacetyl grouping, can be reacted with esters of phosphorous acid, such as tri-lower alkylphosphite compounds, and corresponding phosphono compounds can thus be obtained.

Resulting 3-methylenecepham compounds of the formula I can be converted into 1-oxides of the corresponding 3-methylenecepham compounds by oxidation with suitable oxidising agents, such as those described below. Resulting 1-oxides of 3-methylenecepham compounds of the formula I can be reduced to give the corresponding 3-methylenecepham compounds of the formula I by reduction with suitable reducing agents, such as, for example, those described below. In these reactions it must be borne in mind that, if necessary, free functional groups are protected and are subsequently liberated, if desired.

Suitable oxidising agents for the oxidation of 3-methylenecepham compounds in the 1-position are inorganic per-acids which have a reduction potential of at least +1.5 volt and which consist of non-metallic elements, organic per-acids or mixtures of hydrogen peroxide and acids, especially organic carboxylic acids, having a dissociation constant of at least $10^{116\ 5}$. Suitable inorganic per-acids are periodic acid and persulphuric acid. Organic per-acids are appropriate percarboxylic acids and persulphonic acids which can be added as such or can be formed in situ by the use of at least one equivalent of hydrogen peroxide and of a carboxylic acid. It is desirable to use a large excess of the carboxylic acid if, for example, acetic acid is used as the solvent. Suitable per-acids are, for example, performic acid, peracetic acid, pertrifluoracetic acid, permaleic acid, perbenzoic acid, 3-chloroperbenzoic acid, monoperphthalic acid or p-toluenepersulphonic acid, The oxidation can also be carried out using hydrogen peroxide and catalytic amounts of an acid having a dissociation constant of at least $10^{-5}$, it being possible to employ low concentrations, for example 1–2% or less, but also larger amounts, of the acid. The activity of the mixture above all depends on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, its activity depending on its strength. Acids suitable a catalysts are, for example, acetic acid, perchloric acid and trifluoroacetic acid. Usually, at least equimolar amounts of the oxidising agent, and preferably a small excess of about 10 to about 20%, are used, but larger excess amounts, that is to say up to a 10-fold amount of the oxidising agents or above, can also be used. The oxidation is carried out under mild conditions, for example at temperatures of about −50° to about +100° C, preferably of about −10° C to about +40° C.

The oxidation of 3-methylenecepham compounds to the corresponding 1-oxides can also be carried out by treatment with ozone, as well as with organic hypohalite compounds, such as lower alkyl hypochlorites, for example tert.-butylhypochlorite, which are used in the presence of inert solvents, such as optionally halogenated hydrocarbons, for example methylene chloride, and at temperatures of about −10° to about +30° C, with periodate compounds, such as alkali metal periodates, for example potassium periodate, which are preferably used in an aqueous medium at a pH value of about 6 and at temperatures of about −10° C to about +30° C, with iodobenzene dichloride, which is used in an aqueous medium, preferably in the presence of an organic base, for example pyridine, and with cooling, for example at temperatures of about −20° C to about 0°, or with any other oxidising agent which is suitable for conversion of a thio group into a sulphoxide grouping.

In the 1-oxides of 3-methylenecepham compounds of the formula I, thus obtainable, especially in those compounds in which $R_1^a$, $R_1^b$ and $R_2$ have the abovementioned preferred meanings, the groups $R_1^a$, $R_1^b$ and/or $R_2$ can, within the defined framework, be converted into one another, split off or introduced. A mixture of isomeric α- and β-1-oxides can be separated, for example chromatographically.

The reduction of the 1-oxides of 3-methylenecepham compounds of the formula I can be carried out in a manner which is in itself known, by treatment with a reducing agent, if necessary in the presence of an activating agent. Possible reducing agents are: catalytically activated hydrogen, using noble metal catalysts which contain palladium, platinum or rhodium and which are optionally employed together with a suitable carrier, such as charcoal or barium sulphate; reducing tin, iron, copper or manganese cations, which are used in the form of appropriate compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediamine-tetraacetic acid or nitrilotriacetic acid; reducing dithionite, iodide or ferrocyanide anions which are used in the form of appropriate inorganic or organic salts, such as alkali metal salts, for example sodium dithionite or potassium dithionite, sodium iodide or potassium iodide, or sodium ferrocyanide or potassium ferrocyanide, or in the form of the corresponding acids, such as hydriodic acid; reducing trivalent inorganic or organic phosphorus compounds, such as phosphines, and also esters, amides and halides of phosphinous, phosphonous or phosphorous acids, as well as phosphorus-sulphur compounds corresponding to these phosphorus-oxygen compounds, in which compounds organic radicals above all represent aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane phsophorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, dichlorosilane or trichlorosilane, dibromosilane or tribromosilane, diphenylchlorosilane, dimethylchlorosilane and the like; reducing quaternary chloromethylene-iminium salts, especially chlorides or bromides, wherein the iminium group is substituted by one bivalent or two monovalent organic radicals, such as optionally substituted lower alkylene or lower alkyl groups, such as N-chloromethylene-N,N-diethyliminium chloride or N-chloromethylene-pyrrolidinium chloride; and complex metal hydrides, such as sodium borohydride, in the presence of suitable activating agents, such as cobalt-II chloride, As activating agents which are used together with those of the abovementioned reducing agents which do not themselves possess Lewis acid properties, that is to say which above all are employed together with the dithionite, iodide or ferrocyanide reducing agents and the trivalent phosphorus reducing agents which do not contain halogen, or in the catalytic reduction, there should especially be mentioned organic carboxylic acid halides and sulphonic acid halides, also sulphur halides, phosphorus halides or silicon halides having the same or a greater second order hydrolysis constant than benzoyl chloride, for example phosgene, oxalyl chloride, acetic acid chloride or acetic acid bromide, or chloroacetic acid chloride; pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethyldichlorosilane or trichlorosilane and also suitable acid anhydrides, such as trifluoroacetic acid anhydride, or cyclic sultones, such as ethanesultone, 1,3-propanesultone, 1,4-butanesultone or 1,3-hexanesultone.

The reduction is preferably carried out in the presence of solvents or mixtures thereof, the choice of which is above all determined by the solubility of the starting substances and the choice of the reducing agent, such as, for example, lower alkanecarboxylic acids or esters thereof, such as acetic acid and ethyl acetate, in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofurane or dioxane, ketones, for example acetone, or sulphones, especially aliphatic sulphones, for example dimethylsulphone or tetramethylenesulphone, and the like, together with the chemical reducing agents, these solvents preferably not containing any water. The reaction is usually carried out at temperatures of about −20° to about 100° C, it being possible to carry out the reaction at lower temperatures if very reactive activating agents are used.

Salts of compounds of the formula I and their 1-oxides can be manufactured in a manner which is in itself known. Thus, salts of compounds of the formula I, or of their 1-oxides, which possess acid groups can be formed, for example, by treatment with metal compounds, such as alkali metal salts, or suitable carboxylic acids, for example the sodium salt of α-ethyl-caproic acid, or with ammonia or a suitable organic amine, preferably using stoichiometric amounts or only a small excess of the salt-forming agent. Acid addition salts of compounds of the formula I or of 1-oxides thereof having basic groupings are obtained in the customary manner, for example by treatment with an acid or with a suitable anion exchange reagent. Inner salts of compounds of the formula I or of 1-oxides thereof which contain a slat-forming amino group and a free carboxyl group can be formed, for example, by neutralising salts, such as acid addition salts, to the isoelectric point, for example with weak bases, or by treatment with liquid ion exchangers. Salts of 1-oxides having salt-forming groups can be manufactured analogously.

Salts can be converted into the free compounds in the customary manner, metal salts and ammonium salts, for example, by treatment with suitable acids, and acid addition salts, for example, by treatment with a suitable basic agent.

Resulting mixtures of isomers can be separated into the individual isomers according to methods which are in themselves known, mixtures of diastereomeric isomers, for example, by fractional crystallisation, adsorption chromatography (column chromatography or thin layer chromatography) or other suitable separation processes. Resulting racemates can be separated into the antipodes in the usual manner, if appropriate after introducing suitable salt-forming groupings, for example by forming a mixture of diastereomeric salts with optically active salt-forming agents, separating the mixture into the diastereomeric salts and converting the separated salts into the free compounds, or by fractional crystallisation from optically active solvents.

The process also encompasses those embodiments according to which compounds arising as intermediate products are used as starting substances and the remaining process steps are carried out with these, or the process is stopped at any stage; furthermore, starting substances can be used in the form of derivatives or be formed during the reaction.

Preferably, those starting substances are used, and the reaction conditions are so chosen, that the compounds initially mentioned as being particularly preferred are obtained.

In the conversions, described above, of compounds of the formula I, their 1-oxides or their salts into other compounds of the formula I, their 1-oxides or their salts, care must be taken that such conversions should as far as possible take place in a neutral or acid medium, since under basic conditions the 3-exo-methylene group can be isomerised to a 3-methyl group, with re-arrangement of the double bond to occupy the 3- and especially the 2-position of the cepham ring.

The preparation of the valuable 3-oxo-cepham compounds and 3-hydroxy-cephem and 3-substituted hydroxy-3-cephem compounds which have been mentioned, especially of compounds of the formula II, can be performed as follows, using the compounds of the formula I or their 1-oxides;

A compound obtained according to the invention, of the formula I, in which $R_2$ is a hydroxyl group, a 1-oxide or a salt thereof, is converted by one of the processes described into a compound of the formula

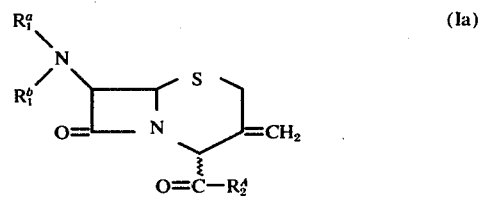

(Ia)

or a 1-oxide thereof, and this is converted oxidatively, according to the process described below, into a cepham-3-one compound of the formula

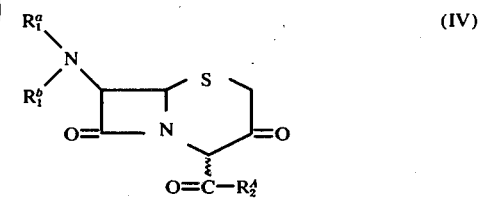

(IV)

or into a corresponding enol with a double bond in the 2,3- or 3,4-position, or a 1-oxide of such a compound.

The oxidative splitting off of the methylene group in compounds of the formula Ia, or 1-oxides thereof, to form an oxo group in the 3-position of the ring skeleton can be carried out in various ways.

It is preferably effected by forming an ozonide intermediate compound by treatment with ozone. Herein, ozone is usually employed in the presence of a solvent, such as an alcohol, for example a lower alkanol, such as methanol or ethanol, a ketone, for example a lower alkanone, such as acetone, an optionally halogenated aliphatic, cycloaliphatic or aromatic hydrocarbon, for example a halogeno-lower alkane, such as methylene chloride or carbon tetrachloride, or a solvent mixture, including an aqueous mixture, and with cooling or slight warming, for example at temperatures of about −90° to about +40° C.

An ozonide formed as an intermediate product is split by reduction, for which it is possible to use catalytically activated hydrogen, for example hydrogen in the presence of a heavy metal hydrogenation catalyst, such as a nickel catalyst or a palladium catalyst, preferably on a suitable carrier, such as calcium carbonate or charcoal, or chemical reducing agents, such as reducing heavy metals, including heavy metal alloys or amalgams, for example zinc, in the presence of a hydrogen donor, such as an acid, for example acetic acid, or an alcohol, for example a lower alkanol, reducing inorganic salts, such as alkali metal iodides, for example sodium iodide, in the presence of a hydrogen donor, such as an acid, for example acetic acid, or reducing organic compounds, such as formic acid, a reducing sulphide compound such as a di-lower alkylsulphide, for example dimethylsulphide, a reducing organic phosphorus compound, such as a phosphine, which can optionally contain substituted aliphatic or aromatic hydrocarbon radicals as substituents, such as tri-lower alkyl-phosphines, for example tri-n-butylphosphine, or triarylphosphines, for example triphenylphosphine, also phosphites which contain optionally substituted aliphatic hydrocarbon radicals as substituents, such as tri-lower alkylphosphites, usually in the form of corresponding alcohol adduct compounds, such as trimethylphosphite, or phosphorous acid triamides which contain optionally substituted aliphatic hydrocarbon radicals as substituents, such as hexa-lower alkylphosphorous acid triamides, for example hexamethyl-phosphorous acid triamide, the latter preferably in the form of a methanol adduct, or tetracyanoethylene. The splitting of the ozonide, which is usually not isolated, is normally carried out under the conditions which are employed for its manufacture, that is to say in the presence of a suitable solvent or solvent mixture, and with cooling or slight warming.

Depending on how the oxidation reaction is carried out, a compound of the formula IV or the corresponding 1-oxide or a mixture of the two compounds is obtained. Such a mixture can be separated into the compound of the formula IV and the corresponding 1-oxide, or can be oxidised to the pure 1-oxide of a compound of the formula IV.

A mixture of a compound of the formula IV with the corresponding 1-oxide can be separated into the individual components in the usual manner, for example by fractional crystallisation or by chromatography (for example column chromatography or thin layer chromatography).

In the conversion of the starting substances of the formula IV or their 1-oxides to the enol derivatives of the formula II or the 1-oxides, it is not necessary to isolate the starting substances of the formula IV or their 1-oxides after they have been manufactured; they can preferably be converted directly into the compounds of the formula II or their 1-oxides in the form of the crude reaction mixture after the manufacture from the compounds of the formula Ia or their 1-oxides.

The compounds of the formula II or their 1-oxides are obtained by converting a cepham-3-one compound of the formula IV or a corresponding enol having a double bond in the 2,3- or 3,4-position, or a 1-oxide of such a compound, into an enol derivative having a functionally modified hydroxyl group of the formula —O—$R_3$ in the 3-position and, if desired, in a resulting compound of the formula II or a 1-oxide thereof, converting the protected carboxyl group of the formula —C(=O)—$R_2^A$ into the free carboxyl group or into another protected carboxyl group and/or, if desired, converting a resulting compound of the formula II, or a 1-oxide thereof, into another compound of the formula II, or a 1-oxide thereof, and/or if desired, converting a resulting compound having a salt-forming group into a salt or a resulting salt into the free compound or into another salt and/or, if desired, separating a resulting isomer mixture into the individual isomers.

Cepham-3-one starting substances of the formula IV or their 1-oxides can be in the keto form and/or in the enol form, with the ring double bond in the latter being in the 2,3- or, preferably, in the 3,4-position. Usually, the starting substances of the formula IV are converted from the enol form into the enol derivatives of the formula II. Furthermore it is also possible, for example, to employ a mixture of a compound of the formula IV and of the corresponding 1-oxide as the starting material and to obtain, as the product, the mixture of a compound of the formula II and of the corresponding 1-oxide.

The conversion of the starting substances of the formula IV, or of 1-oxides thereof, into the enol derivatives can be carried out in a manner which is in itself known.

Enol-ethers, that is to say compounds of the formula II, or 1-oxides thereof, wherein $R_3$ represents an optionally substituted hydrocarbon radical, are obtained according to any process suitable for the etherification of enol groups, it being possible to use starting substances of the formula IV, or 1-oxides thereof, wherein $R_1^a$ and $R_1^b$ represent hydrogen but wherein preferably $R_1^a$ represents an amino protective group $R_1^A$. Preferably, the etherifying reagent used is a diazo compound of the formula $R_3$-$N_2$ (V) corresponding to the optionally substituted hydrocarbon radical $R_3$, or a 1-oxide thereof, above all an optionally substituted diazo-lower alkane, for example diazomethane, diazoethane or diazobutane, and also an optionally substituted phenyl-diazo-lower alkane such as 1-phenyl-diazo lower alkane, for example phenyldiazomethane or diphenyldiazomethane. These reagents are used in the presence of a suitable inert solvent, such as an aliphatic, cycloaliphatic or aromatic hydrocarbon, such as hexane, cyclohexane, benzene or toluene, of a halogenated aliphatic hydrocarbon, for example methylene chloride, of a lower alkanol, for example methanol, ethanol or tert.-butanol, or of an ether, such as of a di-lower alkylether, for example diethyl ether, or of a cyclic ether, for example tetrahydrofuran or dioxane, or of a solvent mixture and, depending on the diazo reagent, with cooling, at room temperature or with slight warming and also, if necessary, in a closed vessel and/or under an inert gas atmosphere, for example a nitrogen atmosphere.

Enol-esters, that is to say compounds of the formula II, wherein $R_3$ represents an acyl group, or 1-oxides thereof, are obtained according to any process suitable for the esterification of enol groups, with at least one of the groups $R_1^a$ and $R_1^b$ in the starting material of the formula IV being different from hydrogen, if simultaneous acylation of a free amino group is to be avoided. Thus, preferably carboxylic acids corresponding to the acyl radical $R_3$, of the formula $R_3$—OH (VI) or reactive acid derivatives thereof are used, such as halides, for example fluorides or chlorides, also pseudohalides, such as cyanocarbonyl compounds corresponding to the carboxylic acids, or anhydrides (by which there are also to be understood the internal anhydrides of carboxylic acids, that is to say ketenes, or of carbamic or thiocarbamic acids, that is to say isocyanates or isothiocyanates, or mixed anhydrides, such as those which can be formed, for example, with halogenoformic acid lower alkyl esters, such as chloroformic acid ethyl esters or isobutyl esters, or with trichloroacetic acid chloride) or activated esters, such as esters with vinylogous alcohols (that is to say enols), for example esters of lower alkanecarboxylic acids with vinylogous alkanols, for example acetic acid isopropenyl ester, the reaction being carried out, if necessary, in the presence of suitable condensation agents, when using acids, for example, in the presence of carbodiimide compounds, such as dicyclohexylcarbodiimide, or carbonyl compounds such as diimidazolylcarbonyl and when using reacting acid derivatives, for example, in the presence of basic agents, such as tri-lower alkylamines, for example triethylamine, or heterocyclic bases, for example pyridine, and when using esters with vinylogous alcohols in the presence of an acid agent, such as a mineral acid, for example sulphuric acid, or a strong sulphonic acid, for example p-toluenesulphonic acid. The acylation reaction can be carried out in the absence or in the presence of a solvent or solvent mixture, with cooling, at room temperature or with warming and, if necessary, in a closed vessel and/or in an inert gas atmosphere, for example a nitrogen atmosphere. Suitable solvents are, for example, optionally substituted, especially optionally chlorinated, aliphatic, cycloaliphatic, or aromatic hydrocarbons such as benzene or toluene, it also being possible to use suitable esterification reagents, such as acetic anhydride, as diluents.

A mixture, obtainable according to the process, of a compound of the formula II and the corresponding 1-oxide can be separated with the aid of suitable methods of separation, for example by chromatography (column chromatography, paper chromatography or plate chromatography), using suitable adsorbents, such as silica gel or aluminium oxide, and eluting agents, and also by fractional crystallisation, solvent distribution and the like. It is also possible to oxidise a mixture of a compound of the formula II and the corresponding 1-oxide directly either to the 1-oxide, or reduce it to a 3-cephem compound of the formula II. These oxidation and reduction steps are described below in relation to the isomerisation of a 2-cephem compound to the corresponding 3-cephem compound, using a 1-oxide as the intermediate product.

Resulting cephem compounds of the formula II wherein the double bond is in the 2,3- or 3,4-position, can be converted into 1-oxides of the corresponding 3-cephem compounds by oxidation with suitable oxidising agents, such as those described below. Resulting 1-oxides of 3-cephem compounds of the formula II, wherein the double bond is in the 3,4-position, can be reduced to the corresponding 3-cephem compounds of the formula II by reduction with suitable reducing agents such as, for example, those described. In these reactions it is necessary to ensure that, if necessary, free functional groups are protected and are subsequently again liberated, if desired.

Cephem compounds obtained can be isomerised. Thus, resulting 2-cephem compounds of the formula II, wherein the double bond is in the 2,3-position, can be converted into the corresponding 3-cephem compounds of the formula II, wherein the double bond is in the 3,4-position, by isomerising a 2-cephem compound of the formula II wherein free functional groups can, if appropriate, be protected transiently, for example as indicated. In this reaction it is possible to use, for example, 2-cephem compounds of the formula II wherein the group of the formula $-C(=O)-R_2$ represents a free or protected carboxyl group, it also being possible to form a protected carboxyl group during the reaction.

Thus it is possible to isomerise a 2-cephem compound of the formula II by treating it with a weakly basic agent and isolating the corresponding 3-cephem compound of the formula II from an equilibrium mixture of the 2- and 3-cephem compounds which may be obtained.

Examples of suitable isomerising agents are organic nitrogen-containing bases, especially tertiary heterocyclic bases of aromatic character, above all bases of the pyridine type, such as pyridine itself, as well as collidines or lutidines, and also quinoline, tertiary aromatic bases, for example those of the aniline type, such as N,N-di-lower alkylanilines, for example N,N-dimethylaniline or N,N-diethylaniline, or tertiary aliphatic, azacycloaliphatic or araliphatic bases, such as N,N,N-tri-lower alkylamines, for example N,N,N-trimethylamine, N,N-dimethyl-N-ethylamine, N,N,N-triethylamine or N,N-diisopropyl-N-ethylamine, N-lower alkyl-azacycloalkanes, for example N-methylpiperidine, or N-phenyl-lower alkyl-N,N-di-lower alkyl-amines, for example N-benzyl-N,N-dimethylamine, as well as mixtures thereof, such as the mixture of a base of the pyridine type, and a N,N,N-tri-lower alkylamine, for example pyridine and triethylamine. Furthermore it is also possible to use inorganic or organic salts of bases, especially of medium-strength to strong bases, with weak acids, such as alkali metal salts or ammonium salts of lower alkanecarboxylic acids, for example sodium acetate, triethylammonium acetate or N-methyl-piperidine acetate, as well as other analogous bases or mixtures of such basic agents.

The above isomerisation with basic agents can be carried out for example, in the presence of a derivative of a carboxylic acid which is suitable for forming a mixed anhydride, such as a carboxylic acid anhydride or carboxylic acid chloride, for example with pyridine in the presence of acetic anhydride. This reaction is preferably carried out in an anhydrous medium, in the presence of absence of a solvent, such as an optionally halogenated, for example chlorinated, aliphatic, cycloaliphatic or aromatic hydrocarbon, or of a solvent mixture, it being possible for bases used as reactants and liquid under the reaction conditions at the same time also to serve as solvents, with cooling, at ambient temperature or with heating, preferably in a temperature range of about $-30°$ to about $+100°$ C, in an inert gas atmosphere, for example a nitrogen atmosphere, and/or in a closed vessel.

The 3-cephem compounds of the formula II, thus obtainable, can be separated from 2-cephem compounds which may still be present, in a manner which is in itself known, for example by adsorption and/or crystallisation.

The isomerisation of 2-cephem compounds of the formula II can also be carried out by oxidising these in the 1-position, if desired separating an isomer mixture of the 1-oxides of 3-cephem compounds of the formula II which may be obtained, and reducing the 1-oxides of the corresponding 3-cephem compounds thus obtainable.

Suitable oxidising agents for the oxidation of 2-cephem compounds in the 1-position are inoganic per-acids which have a reduction potential of at least $+1.5$ volt and which consist of non-metallic elements, organic per-acids or mixtures of hydrogen peroxide and acids, especially organic carboxylic acids, having a dissociation constant of at least $10^{-5}$. Suitable inorganic per-acids are periodic acid and persulphuric acid. Organic per-acids are appropriate percarboxylic acids and persulphonic acids which can be added as such or can be formed in situ by the use of at least one equivalent of hydrogen peroxide and of a carboxylic acid. It is desirable to use a large excess of the carboxylic acid if, for example, acetic acid is used as the solvent. Suitable per-acids are, for example, performic acid, peracetic acid, pertrifluoroacetic acid, permaleic acid, perbenzoic acid, 3-chloroperbenzoic acid, monoperphthalic acid or p-toluenepersulphonic acid.

The oxidation can also be carried out using hydrogen peroxide and catalytic amounts of an acid having a dissociation constant of at least $10^{-5}$, it being possible to employ low concentrations, for example 1-2% or less, but also larger amounts, of the acid. The activity of the mixture above all depends on the strength of the acid. Examples of suitable mixtures are those of hydrogen peroxide with acetic acid, perchloric acid or trifluoroacetic acid.

The above oxidation can be carried out in the presence of suitable catalysts. Thus, for example, the oxidation with percarboxylic acid can be catalysed by the presence of an acid having a dissociation constant of at least $10^{-5}$, its activity depending on its strength. Acids suitable as catalysts are, for example, acetic acid, perchloric acid and trifluoroacetic acid. Usually, at least equimolar amounts of the oxidising agent, and preferably a small excess of about 10 to about 20%, are used, but larger excess amounts, that is to say up to a 10-fold amount of the oxidising agent or above, can also be use. The oxidation is carried out under mild conditions, for example at temperatures of about $-50°$ to about $+100°$ C, preferably of about $-10°$ to about $+40°$ C.

The oxidation of 2-cephem compounds to the 1-oxides of the corresponding 3-cephem compounds can also be carried out by treatment with ozone, as well as with organic hypohalite compounds, such as lower alkyl hypochlorites, for example tert.-butylhypochlorite, which are used in the presence of inert solvents, such as optionally halogenated hydrocarbons, for example methylene chloride, and at temperatures of about $-10°$ to about $+30°$ C, with periodate compounds, such as alkali metal periodates, for example potassium periodate, which are preferably used in an aqueous medium at a pH value of about 6 and at temperatures of about $-10°$ C to about $+30°$ C, with iodobenzene dichloride, which is used in an aqueous medium, preferably in the presence of an organic base, for example pyridine, and with cooling, for example at temperatures of about $-20°$ C to about $0°$, or with any other oxidising agent which is suitable for conversion of a thio group into a sulphoxide grouping.

In the 1-oxides of 3-cephem compounds of the formula II, thus obtainable, especially in those compounds in which $R_1^a$, $R_1^b$ and $R_2$ have the abovementioned preferred meanings, the groups $R_1^a$, $R_1^b$ and/or $R_2$ can, within the defined framework, be converted into one another, split off or introduced. A mixture of isomeric $\alpha$- and $\beta$-1-oxides can be separated, for example chromatographically.

The reduction of the 1-oxides of ceph-3-em compounds of the formula II can be carried out in a manner which is in itself known, by treatment with a reducing agent, if necessary in the presence of an activating agent. Possible reducing agents are: catalytically activated hydrogen, using noble metal catalysts which contain palladium, platinum or rhodium and which are optionally employed together with a suitable carrier, such as charcoal or barium sulphate; reducing tin, iron, copper or manganese cations, which are used in the form of appropriate compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediaminetetraacetic acid or nitrilotriacetic acid; reducing dithionite, iodide or ferrocyanide anions which are used in the form of appropriate inorganic or organic salts, such as alkali metal salts, for example sodium dithionite or potassium dithionite, sodium iodide or potassium iodide, or sodium ferrocyanide or potassium ferrocyanide, or in the form of the corresponding acids, such as hydriodic acid; reducing trivalent inorganic or organic phosphorus compounds, such as phosphines, and also esters, amides and halides of phosphinous, phosphonous or phosphorous acids, as well as phosphorus-sulphur compounds corresponding to these phosphorus-oxygen compounds, in which compounds organic radicals above all represent aliphatic, aromatic or araliphatic radicals, for example optionally substituted lower alkyl, phenyl or phenyl-lower alkyl groups, such as, for example, triphenylphosphine, tri-n-butylphosphine, diphenylphosphinous acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, dichlorosilane or trichlorosilane, dibromosilane or tribromosilane, diphenylchlorosilane, dimethylchlorosilane and the like; reducing quaternary chloromethylene-iminium salts, especially chlorides or bromides, wherein the iminium group is substituted by one bivalent or two monovalent organic radicals, such as optionally substituted lower alkylene or lower alkyl groups, such as N-chloromethylene-N,N-diethyliminium chloride or N-chloromethylene-pyrrolidinium chloride; and complex metal hydrides, such as sodium borohydride, in the presence of suitable activating agents, such as cobalt-II chloride.

As activating agents which are used together with those of the abovementioned reducing agents which do not themselves possess Lewis acid properties, that is to say which above all are employed together with the dithionite, iodide or ferrocyanide reducing agents and the trivalent phosphorus reducing agents which do not contain halogen, or in the catalytic reduction, there should especially be mentioned organic carboxylic acid halides and sulphonic acid halides, also sulphur halides, phosphorus halides or silicon halides having the same or a greater second order hydrolysis constant than benzoyl chloride, for example phosgene, oxalyl chloride, acetic acid chloride or acetic acid bromide, or chloroacetic acid chloride; pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethyldichlorosilane or trichlorosilane and also suitable acid anhydrides, such as trifluoroacetic acid anhydride, or cyclic sultones, such as ethanesultone, 1,3-propanesultone, 1,4-butanesultone or 1,3-hexanesultone.

The reduction is preferably carried out in the presence of solvents or mixtures thereof, the choice of which is above all determined by the solubility of the starting substances and the choice of the reducing agent, such as, for example, lower alkanecarboxylic acids or esters thereof, such as acetic acid and ethyl acetate, in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofurane or dioxane, ketones, for example acetone, or sulphones, especially aliphatic sulphones, for example dimethylsulphone or tetramethylenesulphone, and the like, together with the chemical reducing agents, these solvents preferably not containing any water. The reaction is usually carried out at temperatures of about −20° to about 100° C, it being possible to carry out the reaction at lower temperatures if very reactive activating agents are used.

In the 3-cephem compounds of the formula II, thus obtainable, $R_1{}^a$, $R_1{}^b$ and/or $R_2$ can be converted into other groups $R_1{}^a$, $R_1{}^b$ or $R_2$ as described above, it being necessary to bear in mind that the 3-cephem compounds are considerably more sensitive towards basic agents than the corresponding 2-cephem compounds.

The pharmacologically usable compounds obtainable from the compounds of the formula I or their 1-oxides which can be manufactured according to the invention can, for example, be used for the manufacture of pharmaceutical preparations which contain an effective amount of the active substance together with, or mixed with, inorganic or organic, solid or liquid, pharmaceutically usable excipients which are suitable for enteral administration or preferably for parenteral administration. Thus, tablets or gelatine capsules are used which contain the active substance together with diluents, for example lactose, dextrose, sucrose, mannitol sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminum silicate, starches, such as corn starch, wheat starch, rice starch or arrowroot starch, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorbents, dyestuffs, flavouring substances and sweeteners. The pharmacologically active compounds are preferably used in the form of injectable preparations, for example preparations which can be administered intravenously, or of infusion solutions. Such solutions are, preferably, isotonic aqueous solutions or suspensions and these can, for example, be manufactured before use from lyophilised preparations which contain the active substance by itself or together with an excipient, for example mannitol. The pharmaceutical preparations can be sterilised and/or contain auxiliaries, for example preservatives, stabilisers, wetting agents or emulsifiers, solubilising agents, salts for regulating the osmotic pressure and/or buffers. The present pharmaceutical preparations which can, if desired, contain further pharmacologically valuable substances, are manufactured in a manner which is in itself known, for example by means of conventional mixing, granulating, dragée-making, dissolving or lyophilising processes, and contain from about 0.1 to 100%, especially from about 1 to about 50%, of lyophilised products or up to 100% of the active substance.

In the context of the present description, the organic radicals described as "lower" contain, unless expressly defined, up to 7, preferably up to 4, carbon atoms; acyl radicals contain up to 20, and preferably up to 12, carbon atoms.

The examples which follow serve to illustrate the invention.

EXAMPLE 1

A solution of 3.3 g of approx. 90 percent strength (5.6 mmols) sodium salt of 7β-(D-α-tert.-butoxycarbonylamino-α-phenylacetylamino)-cephalosporanic acid in 80 ml of 0.5 M aqueous potassium phosphate buffer (pH 7) and 8 ml of dimethylformamide is adjusted to pH 6.0 with concentrated phosphoric acid. The aluminum amalgam obtained from 3.3 g of aluminum grit is added thereto and the mixture is stirred for 30 minutes at 45° C and pH 6.0 (kept constant by addition of phosphoric acid). It is diluted with 100 ml of ice, covered with a layer of cold ethyl acetate, and adjusted to pH 2.0 with concentrated phosphoric acid. After saturation with sodium chloride, the organic layer is separated off and the residue is twice re-extracted with ethyl acetate. The extracts are washed with saturated sodium chloride solution, dried over sodium sulphate and evaporated to give 3.55 g of a greenish foam which is caused to crystallise in 9 ml of ethyl acetate. The mixture is slowly diluted with 15 ml of ethyl acetate/hexane, 2:3, and filtered after standing for 2 hours at −5° C, and 3-methylene-7β-(D-αtert.-butoxycarbonylamino-α-phenylacetylamino)-cepham-4α-carboxylic acid, melting point 196–7° C (corrected) is obtained; $[\alpha]_D^{20} = +35° \pm 1°$ (C = 1.0; 5N sodium bicarbonate). IR-spectrum (Nujol): 2.98; 5.67; 5.74; 5.92; 6.01; 6.55; 6.62; 7.50; 8.01; 8.32; 8.56; 9.51; 10.77; 11.36 and 11.82 μm. Thin layer chromatogram on silica gel: Rf = 0.58 (system 52/n-butanol-glacial acetic acid-water, 75:7.5:21) and Rf = 0.35 (system 100/ethyl acetate-pyridine-glacial acetic acid-water, 60:20:6:11).

The sodium salt of 7β-(D-α-tert.-butoxycarbonylamino-α-phenylacetylamino)-cephalosporanic acid, employed as the starting material, is prepared by dissolving 50 g of crude 7β-(D-α-tert.-butoxycarbonylamino-α-phenylacetylamino)-cephalosporanic acid, obtained according to J.L. Spencer et al., Journal of Medicinal Chemistry 9, 746 (1966), in 170 ml of dioxane, diluting the solution with 170 ml of ethyl acetate, and slowly adding 50 ml of a 50 percent strength solution of sodium α-ethylhexanoate in methanol, whilst cooling. The salt is filtered off, washed with dioxaneethyl acetate, 2:1, and pure ethyl acetate, and digested with 1 l of ether and then with 200 ml of ethanol.

The aluminum used is converted to an amalgam as follows: 3.3 g of aluminum grit are swirled for 30 seconds in 100 ml of 5 percent strength sodium hydroxide solution and after decanting are washed 3 times with 300 ml of water at a time. The metal is then treated for 3 minutes with 130 ml of 0.5 percent strength mercury-(II) chloride solution and washed 3 times with 300 ml of water at a time. The entire procedure is repeated once and the amalgam is finally washed 3 times with tetrahydrofurane. Approx. 15 ml of ethyl acetate are used to transfer the amalgam into the reaction vessel.

EXAMPLE 2

30 g (53 mmols) of pure ethanolamine salt of 7β-(D-α-tert.-butoxycarbonylamino-phenylamino)-cephalosporanic acid, in 750 ml of 0.5 M potassium phosphate buffer (pH 7) and 75 ml of dimethylformamide are stirred, analogously to Example 1, with the amalgam prepared from 50 g of aluminum as in Example 1, for 30 minutes at 45° C and pH 5.5. Analogous working up gives crystalline 3-methylene-7β-(Dα-tert.-butoxycarbonylamino-phenylacetylamino)-cepham-4α-carboxylic acid.

The ethanolamine salt used as the starting material is obtained as follows: a solution of 3.6 ml of ethanolamine in 30 ml of methanol is added at 0° C to a solution of 30 g of 7β-(D-α-tert.-butoxycarbonylamino-phenylacetylamino)cephalosporanic acid in 150 ml of methanol and the salt which has separated out is filtered off after 30 minutes.

EXAMPLE 3

202 g (0.4 mol) of crystalline 7β-(D-α-tert.-butoxycarbonylamino-phenylacetylamino)-cephalosporanic acid, melting point 130°–132° C (corrected) are largely dissolved in 4.5 l of 0.5 M potassium phosphate buffer (pH 7) and 450 ml of dimethylformamide in a 10 l reaction vessel, whilst stirring. The pH is adjusted to 6.0 by adding concentrated phosphoric acid and the amalgam obtained from 200 g of aluminum grit (for preparation see below) is added. 0.5 l of ethyl acetate is added and the temperature of the mixture is allowed to rise to 40° C over the course of 10 minutes through the exothermicity, without application of cooling. By occasionally cooling with an ice bath, the temperature is brought to 46° C over the course of a further 10 minutes, and is kept constant thereat. After 15 minutes at 46° C, the mixture is cooled to 29° C (acetone/solid carbon dioxide bath) over the course of 10 minutes, and is poured onto 3 kg of ice and 5 l of ice-cold ethyl acetate. The mixture is acidified to pH 2 with concentrated phosphoric acid, whilst stirring, and is saturated with sodium chloride. After phase separation, the aqueous phase is re-extracted twice with 4 l of cold ethyl acetate at a time.

The organic phases are washed once with 4 l of cold saturated sodium chloride solution, dried over magnesium sulphate and concentrated to approx. 1 l in vacuo. The incipient crystallisation of the product is completed by standing for 3 hours in a refrigerator. Filtration and drying yield crystalline 3-methylene-7β-(D-α-tert.-butoxycarbonylamino-phenylacetylamino)-4α-carboxylic acid.

The amalgam used is prepared as follows: 200 g of aluminum grit are covered with 2 l of 5 percent strength aqueous sodium hydroxide solution and etched for 40 seconds whilst swirling the mixture. The liquid is decanted and the aluminum is washed twice with water. The residue is treated for 3 minutes with 2 l of 0.5 percent strength aqueous mercury-(II) chloride solution whilst swirling, the solution is decanted and the residue is again shaken for 3 minutes with a further 2 l of mercury-(II) chloride solution. After decanting and washing 3 times with water, the amalgam is immediately employed as a reducing agent.

EXAMPLE 4

A solution of 19.5 g of 7β-(α-phenylacetylamino)-cephalosporanic acid in 400 ml of 0.5 M phosphate buffer (pH7) (without added dimethylformamide) is stirred with 20 g of aluminum amalgam for 30 minutes at 45° C and pH 5.7. The ethyl acetate extract obtained at pH 2 contains 16 g of crude 3-methylene-7β-(α-phenylacetylamino)-cepham-4-carboxylic acid; thin layer chromatogram; Rf (system 52): 0.56; Rf (system 100): 0.67.

A solution of diphenyldiazomethane in acetone is added in portions over the course of 1 hour to a solution of a crude product in acetone, until a red colouration persists. After adding 2 ml of glacial acetic acid and 300 ml of toluene, the mixture is evaporated and the residue is chromatographed on 800 g of silica gel (Merck). 3-Methylene-7β-(α-phenylacetylamino-cepham-4-carboxylic acid benzhydryl ester of melting point 133–6° C crystallises from the 1 l fraction eluted with toluene-ethyl acetate, 7:3; thin layer chromatogram Rf (toluene-ethyl acetate, 3:1); 0.43.

EXAMPLE 5

A solution of 8 g of 3-methylene-7β-(D-α-tert.butoxycarbonylamino-α-phenylacetylamino)-cepham-4α-carboxylic acid in 100 ml of methanol is stirred for 1 hour at room temperature with a solution of 6 g of diphenyldiazomethane in 30 ml of benzene. The crude product obtained after evaporation is chromatographed on 500 g of silica gel; 3-methylene-7β-(D-α-tert.-butoxycarbonylamino-α-phenylacetyl-amino)-cepham-4α-carboxylic acid diphenylmethyl ester is eluted with a 4:1 mixture of petroleum ether; after crystallisation from a mixture of methylene dichloride and hexane, the product melts at 156°–158° C; $[\alpha]_D = -50° \pm 1°$ (C = 0.713, chloroform); ultraviolet absorption spectrum in 95% strength aqueous ethanol; $\lambda_{max} = 258 \mu$ ($\epsilon = 990$); infrared absorption spectrum (in methylene chloride): characteristic bands at 2.94 μ, 5.64 μ, 5.74 μ, 5.88 μ (shoulder) and 6.71 μ.

EXAMPLE 6

3-Methylene-7β-(α-phenylacetylamino)-cepham-4α-carboxylic acid diphenylmethyl ester can be obtained analogously to the description in Example 5, starting from 3-methylene-7β-(α-phenylacetylamino)-cepham-4α-carboxylic acid. Melting point 144°–147° C (methylene chloride-hexane); $[\alpha]_D{}^{20} = -18° \pm 1°$ (c = 0.715 in chloroform); ultraviolet absorption spectrum (in 95% strength aqueous ethanol): $\lambda_{max} = 254$ mμ ($\epsilon = 1,540$) and 260 mμ ($\epsilon = 1,550$); infrared absorption spectrum (in methylene chloride): characteristic bands at 2.94 μ, 5.65 μ, 5.74 μ, 5.94 μ, 6.26 μ and 6.67 μ.

EXAMPLE 7

3.2 ml of absolute pyridine and 32 ml of an 8% strength solution of phosphorus pentachloride in methylene chloride are added to a solution, cooled to −15° C, of 2.0 g of 3-methylene-7β-(α-phenylacetylamino)-cephem-4α-carboxylic acid diphenylmethyl ester in 80 ml of absolute methylene chloride and the mixture is stirred for one hour under a nitrogen atmosphere at a temperature between −10° and −5° C. The reaction mixture is then cooled to −25° C, 25 ml of absolute methanol are added and the mixture is stirred for 1 hour at −10° C and then for 1.5 hours at room temperature. 80 ml of an 0.5 molar aqueous solution of potassium dihydrogen phosphate are then added, the pH value is adjusted to 2 with 20% strength aqueous phosphoric acid and the mixture is stirred for 30 minutes at room temperature.

The organic phase is separated off; the aqueous phase is twice re-extracted with 150 ml of methylene chloride at a time and the organic solutions are combined, dried over sodium sulphate and evaporated. The oily residue is taken up in 25 ml of ethyl acetate and a solution of 1.14 g of 4-methylphenylsulphonic acid monohydrate in 25 ml of ethyl acetate is added at 0° C. A voluminous precipitate separates out, which is filtered off, rinsed with cold ethyl acetate and diethyl ether, dried and recrystallised from a mixture of methylene chloride and diethyl ether. The 4-methylphenylsulphonate of 7β-amino-3-methylene-cepham-4α-carboxylic acid diphenylmethyl ester is thus obtained in the form of colourless needles, melting point 153°–155° C; $[\alpha]_D = 14° \pm 1°$ (c = 0.97 in methanol); ultraviolet absorption spectrum (in ethanol): $\lambda_{max} = 257$ μ (μ = 1,500); infrared absorption spectrum (in methylene chloride): characteristic bands at 3.5 μ, 5.60 μ, 5.73 μ, 8.50 μ, 9.68 μ and 9.92 μ.

EXAMPLE 8

An oxygen/ozone stream containing 0.21 mmol of ozone/minute, is passed for 1 hour, with vigorous stirring, into a solution, cooled to −70° C, of 5.0 g of 3-methylene-7β-(D-α-tert.-butoxycarbonylamino-α-phenylacetylamino)-cepham-4α-carboxylic acid diphenylmethyl ester in 500 ml of methylene chloride. After a further 10 minutes, 3 ml of dimethyl sulphide are added to the reaction mixture, and the whole is stirred for 1 hour at −65° C and for 2 hours at room temperature and then evaporated under reduced pressure. The crude product, which contains 7β-(D-α-tert.-butoxycarbonyl-amino-α-phenylacetyl-amino)-cepham-3-one-4ξ-carboxylic acid diphenylmethyl ester, in 150 ml of methanol, is treated at 0° C with an excess of a solution of diazomethane in diethyl ether and the mixture is stirred for 15 minutes and then evaporated. A yellowish foam is obtained, which is chromatographed on 200 g of silica gel. Amorphous 3-methoxy-7β-(D-α-tert.-butoxycarbonylamino-α-phenylacetyl-amino)-3-cephem-4-carboxylic acid diphenylmethyl ester is eluted with a 3:1 mixture of toluene and ethyl acetate. Thin layer chromatogram (silica gel): Rf = 0.22 (system: toluene/ethyl acetate, 3:1); infrared-absorption spectrum (in methylene chloride): characteristic bands at 2.94 μ, 5.62 μ, 5.84 μ, 5.88 μ, 6.25 μ and 6.70 μ. Ultraviolet absorption spectrum (in ethanol): $\lambda_{max}$=264 μ (ε = 6,500); $[\alpha]_D^{20} = 1° \pm$ '°(C = 0.98; CHCl$_3$).

EXAMPLE 9

Analogously, starting from 3-methylene-7β-(α-phenylacetylamino)-cepham-4α-carboxylic acid diphenylmethyl ester, it is possible to obtain amorphous 7β-(α-phenylacetylamino)cepham-3-one-4ξ-carboxylic acid diphenylmethyl ester [thin layer chromatography (silica gel): Rf~0.47 (system: toluene/acetone /methanol/acetic acid, 80:10:5:5); infrared absorption spectrum (in methylene chloride): characteristic bands at 2.95 μ, 5.61 μ, 5.77 μ, 5.93 μ, 6.21 μ and 6.63 μ; ultraviolet absorption spectrum (in ethanol): $\lambda_{max} = 283$ μ (ε = 4,350). THe compound shows a positive iron-II chloride reaction which indicates the presence of the enol form]. From this compound, 3-methoxy-7β-(α-phenylacetylamino)-3-cephem-4-carboxylic acid diphenylmethyl ester can be obtained, ultraviolet absorption spectrum (in ethanol): $\lambda_{max} = 264$ μ (ε =6,400); infrared absorption spectrum (in methylene chloride): characteristic bands at 2.94 μ, 5.63 μ, 5.83 μ, 5.94μ, 6.26 μ and 6.68 μ.

EXAMPLE 10

A mixture of 8.8 g of 3-methoxy-7β-(D-α-tert.-butoxycarbonylamino-α-phenyl-acetylamino)-3-cephem-4-carboxylic acid diphenylmethyl ester, 8.6 ml of anisole and 145 ml of trifluoroacetic acid is stirred for 15 minutes at 0° C, 400 ml of precooled toluene are then added and the whole is evaporated under reduced pressure. The residue is dried in a high vacuum, digested with diethyl ether and filtered off. The trifluoroacetate of 3-methoxy-7β-(D-α-phenyl-glycylamino)-3-cephem-4-carboxylic acid, is thus obtained in a pulverulent form and is dissolved in 20 ml of water. The solution is twice washed with 25 ml of ethyl acetate at a time and the pH value is adjusted to about 5 with a 20% strength solution of triethylamine in methanol whereupon a colourless precipitate forms. The mixture is stirred for one hour in an ice bath, 20 ml of acetone are then added and the whole is left to stand for 16 hours at about 4° C. The colourless precipitate is filtered off, washed with acetone and diethyl ether and dried under reduced pressure. 3-Methoxy-7β-(D-α-phenyl-glycylamino)-3-cephem-4-carboxylic acid is thus obtained, in the form of a micro-crystalline powder, as the inner salt which in addition is in the form of a hydrate, melting point 174°–176° C (with decomposition); $[\alpha]_D^{20} = +149°$ (c = 1,03 in 0.1 N hydrochloric acid); thin layer chromatogram (silica gel; development with iodine): Rf~0.36 (system: n-butanol/pyridine/acetic acid/water, 40:24:6:30); ultraviolet absorption spectrum (in 0.1 N aqueous sodium bicarbonate solution): $\lambda_{max} = 267$ μ (ε = 6,200); infrared absorption spectrum (in mineral oil): characteristic bands inter alia at 5.72 μ, 5.94 μ, 6.23 μ and 6.60 μ.

EXAMPLE 11

A mixture of 0.06 g of 3-methoxy-7β-phenylacetylamino-3-cephem-4-carboxylic acid diphenylmethyl ester, 0.05 ml of anisole and 1 ml of trifluoroacetic acid is left to stand for 5 minutes at room temperature and is then evaporated under reduced pressure. The residue, together with a 1:1 mixture of chloroform and toluene is twice evaporated to dryness and chromatographed on 5 g of silica gel (containing about 5% of water). Amorphous 3-methoxy-7β-(α-phenylacetylamino)-3-cephem-4-carboxylic acid is eluted with methylene chloride containing 30–50% of acetone and lyophilised from dioxane; ultraviolet absorption spectrum (in 95% strength aqueous ethanol): $\lambda_{max}=265$ μ (ε=5,800); infrared absorption spectrum (in methylene chloride): characteristic bands at 3.03 μ, 5.66 μ, 5.90 μ, 6.24 μ and 6.50 μ; $[\alpha]_D^{20} =+110° \pm 1°$ (C = 0.740; dioxane).

EXAMPLE 12

40 g of aluminum amalgam are added to a solution of 21.8 g (80 mmols) of 7β-aminocephalosporanic acid in 900 ml of 0.5 M phosphate buffer (pH 7) and 100 ml of dimethylformamide. The mixture is stirred for 1 hour at pH 6.0 and 45° C. After cooling, the reaction mixture is washed with cold ethyl acetate and the aqueous phase is filtered through celite. The filtrate is adjusted to pH 3.5 and evaporated in vacuo and the residue is taken up in 200 ml of methanol-water, 7:3. The portion filtered off (27.5 g) still contains considerable amounts of inorganic salts in addition to the product. 7β-Amino-3-methylene-cepham-4α-carboxylic acid is obtained as an almost colourless powder by shaking with 150 ml of water, leaving the mixture to stand for 3 hours at 0° C, and filtering. Thin layer chromatogram on silica gel: Rf (system 52/n-butanol-glacial acetic acid-water 75:75:21 ) = 0.20, Rf (system 100/ethyl acetate-pyridine-glacial acetic acid-water, 60:20:6:11) = 0.13, Rf (system 200/n-butanol-carbon tetrachloride-methanol-formic acid-water, 30:40:20:5:5) = 0.34.

EXAMPLE 13

7β-Amino-3-methylene-cepham-4α-carboxylic acid benzhydryl ester (Example 7) is split in trifluoroacetic acid solution for 5 minutes at 20° C to give the free acid. The mixture is evaporated, the residue is taken up in toluene and the mixture is again evaporated, giving 7β-amino-3-methylene-cepham-4α-carboxylic acid.

EXAMPLE 14

A solution of 2.5 g of N-tert.-butoxycarbonyl-D-α-phenylglycine in 30 ml of tetrahydrofurane and 1.4 ml of triethylamine is mixed with 1.3 ml of chloroformic acid isobutyl ester at −10° C and the mixture is stirred for 20 minutes at −10° C. An ice-cold solution of 2.1 g of 7β-amino-3-methylene-cepham-4-carboxylic acid in 40 ml of 0.5 M dipotassium hydrogen phosphate solution is rapidly poured into the former mixture. The whole is stirred for ½ hour at 0° C and ½ hour at 25° C, the tetrahydrofurane is evaporated off and the aqueous phase is washed with ether. Extraction at pH 2.0 with ethyl acetate and crystallisation from ethyl acetate-hexane gives 3-methylene-7β-(D-α-tert.-butoxycarbonylamino-α-phenylacetylamino)-cepham-4α-carboxylic acid.

EXAMPLE 15

A solution of diazomethane in diethyl ether is added to a solution of 0.50 g of the 4-methylphenylsulphonate of 7β-amino-cepham-3-one-4ξ-carboxylic acid diphenylmethyl ester, which is largely in the enol form, that is to say in the form of the 4-methylphenylsulphonate of 7β-amino-3-cepham-3-ol-4-carboxylic acid diphenylmethyl ester, in 25 ml of methanol at 0° C, until a yellow colouration persists. The mixture is stirred for 10 minutes in an ice bath and is then evaporated. The residue is chromatographed on silica gel. Oily 7β-amino-3-methoxy-3-cepham-4-carboxylic acid diphenylmethyl ester is eluted with a 2:1 mixture of toluene and ethyl acetate. Thin layer chromatogram (silica gel; development with iodine vapour): RF~0.39 (system: ethyl acetate); ultraviolet absorption spectrum (in ethanol): $\lambda_{max} = 265$ μ ($\epsilon = 6,100$); infrared absorption spectrum (in methylene chloride): characteristic bands at 3.33 μ, 5.63 μ, 5.81 μ and 6.23 μ.

The further elution with ethyl acetate gives oily 7βdimethylamino-3-methoxy-3-cepham-4-carboxylic acid diphenylmethyl ester, thin layer chromatogram (silica gel; development with iodine vapour): Rf~0.20 (system: ethyl acetate); ultraviolet absorption spectrum (in ethanol): $\lambda_{max} = 265$ μ ($\epsilon = 5,900$); infrared absorption spectrum (in methylene chloride): characteristic bands at 2.98 μ, 3.33 μ, 5.62 μ, 5.81 μ and 6.24 μ.

The starting material can be prepared as follows:

3.2 ml of absolute pyridine and 32 ml of an 8% strength solution of phosphorus pentachloride in methylene chloride are added to the solution, cooled to −15° C, of 2.0 g of 3-methylene-7β-phenylacetylamino-cepham-4α-carboxylic acid diphenylmethyl ester in 80 ml of absolute methylene chloride and the mixture is stirred for one hour under a nitrogen atmosphere at a temperature between −10° and −5° C. The reaction mixture is then cooled to −25° C, 25 ml of absolute methanol are added and the whole is stirred for 1 hour at −10° C and then for 1.5 hours at room temperature. 80 ml of an 0.5 molar aqueous solution of potassium dihydrogen phosphate are then added, the pH value is adjusted to 2 with 20% strength aqueous phosphoric acid and the mixture is stirred for 30 minutes at room temperature.

The organic phase is separated off; the aqueous phase is twice re-extracted with 150 ml of methylene chloride at a time and the organic solutions are combined, dried over sodium sulphate and evaporated. The oily residue is taken up in 25 ml of ethyl acetate and a solution of 1.14 g of 4-methylphenylsulphonic acid monohydrate in 25 ml of methylene chloride is added at 0 C. A voluminous precipitate separates out, which is filtered off, rinsed with cold ethyl acetate and diethyl ether, dried and recrystallised from a mixture of methylene chlorie and diethyl ether. The 4-methylphenylsulphonate of 7β-amino-3-methylene-cepham-4α-carboxylic acid diphenylmethyl ester is thus obtained in the form of colourless needles, melting point 153°–155° C; $[\alpha]_D = -14° \pm 1°$ (c = 0.97 in methanol); ultraviolet absorption spectrum (in ethanol): $\lambda_{max} = 257$ μ ($\epsilon = 1,500$); infra-red absorption spectrum (in methylene chloride): characteristic bands at 3.5 μ, 5.60 μ, 5.73 μ, 8.50 μ, 9.68 μ and 9.92 μ.

A stream of oxygen and ozone (containing 0.35 mmol of ozone per minute) is passed for 4 minutes through a solution, cooled to −60° C, of 0.553 g of the 4-methylphenylsulphonate of 7β-amino-3-methylene-cepham-4α-carboxylic acid diphenylmethyl ester in 50 ml of methanol. After a further 5 minutes, 0.3 ml of dimethyl sulphide is added to the solution which is pale blue in colour. The mixture is stirred for 15 minutes at −70° C, for 1 hour at −12° C and for one hour in an ice bath and is then evaporated. The residue is taken up in a small quantity of methylene chloride, diethyl ether is then added until the mixture turns cloudy, and the mixture is left to stand. The micro-crystalline pulverulent precipitate, which is reddish in colour, is filtered off and gives the 4-methylphenylsulphonate of 7β-amino-cepham-3-one-4α-carboxylic acid diphenylmethyl ester, which is principally in the enol form as the 4-methylphenylsulphonate of 7β-amino-3-cephem-3-ol-4-carboxylic acid diphenylmethyl ester, melting point 143°–145° C (with decomposition); thin layer chromatogram (silica gel) Rf~0.28 (system: ethyl acetate/pyridine/water, 85:10:5); ultraviolet absorption spectrum (in ethanol): $\lambda_{max} = 262$ mμ ($\epsilon = 3,050$) and 282 mμ ($\epsilon = 3,020$); infrared absorption spectrum (in methylene chloride): characteristic bands at 5.58 μ, 5.77 μ (shoulder), 6.02 μ and 6.22 μ.

EXAMPLE 16

1 ml of pyridine and 0.5 ml of phenylacetic acid chloride are added at 0° C, under a nitrogen atmosphere, to a suspension of 0.250 g of 7β-amino-3-methoxy-3-cephem-4-carboxylic acid diphenylmethyl ester in 25 ml of methyl chloride and the mixture is stirred for 30 minutes at this temperature. The reaction mixture is evaporated under reduced pressure; the residue is stirred for 10 minutes with 20 ml of a 1:1 mixture of dioxane and water and diluted with methylene chloride. The aqueous phase is separated off and extracted with methylene chloride. The combined organic phases are washed with a saturated aqueous sodium bicarbonate solution and a saturated aqueous sodium chloride solution, dried over sodium sulphate and evaporated under reduced pressure. The crude product is purified by means of preparative thin layer chromatography using, as the solvent, a 1:1 mixture of toluene and ethyl acetate. The zone visible under ultraviolet light of λ = 254 mμ (Rf~0.35) is eluted with a 4:1 mixture of acetone and methanol and gives 3-methoxy-7β-(α-phenylacetylamino)-3-cephem-4-carboxylic acid diphenylmethyl ester which is identical with the product obtainable by the process of Example 9.

EXAMPLE 17

A solution of 4.7 g of N-benzoyl-oephlosporin C in 85 ml of 0.5 M phosphate buffer (pH 7) and 9 ml of dimethylformamide is stirred with 4.7 g of aluminium amalgam for 45 minutes at pH 6.0 and 45° C. Working up analogously to Example 1, and crystallisation from ethyl acetate-ether, 1:4, gives 3-methylene-7β-(5-benzoylamino-adipoylamino)-cepham-4α-carboxylic acid, melting point 82°–89° C with decomposition. Thin layer chromatogram on silica gel: Rf (system 52/n-butanol-glacial acetic acid-water, 75:7.5:21):0.53, Rf (system 100/ethyl acetate-pyridine-glacial acetic acid-water, 60:20:6:1):0.08.

To manufacture the starting material, 50 g of the sodium salt of cephalosporin C are dissolved in 1.5 l of 10 per cent strength dipotassium hydrogen phosphate solution, 1.2 l of acetone are added, and at 0° C 21 g of benzoyl chloride are added. The mixture is stirred for 30 minutes at 0° C and 45 minutes at 20° C, whilst keeping the pH constant at 8.5 by addition of 50 per cent strength tripotassium phosphate solution. The mixture is concentrated to approx. half its volume, washed with ethyl acetate, acidified to pH 2.0 and extracted with ethyl acetate. The evaporation residue is crystallised from acetone and N-benzoyl-cephalosporin C, melting point 117°–119° C, is obtained. Thin layer chromatogram: Rf (system 52): 0.37; (system 100): 0.08.

EXAMPLE 18

The amalgam from 2.2 g of aluminum grit is added to a solution of 2.24 g of N-benzoyl-desacetyl-cephalosporin C-lactone in 55 ml of 0.5 M potassium phosphate buffer of pH 7 and 5 ml of dimethylformamide, and the mixture is stirred for 30 minutes at pH 6.0 and 45° C. Working up analogously to Example 1, and crystallisation from ethyl acetate, gives 3-methylene-7β-(5-benzoylamino-adipoylamino)-cepham-4α-carboxylic acid, which is identical with the compound obtained according to Example 17.

The starting material is obtained by neutralising 15 g of N-benzoyl-cephalosporin C (see Exaample 17) in 75 ml of water with approx. 25 ml of 2 normal sodium hydroxide solution to pH 7.5, adding 0.5 g of enriched enzyme from Bacillus subtilis A7 CC 6633 (compare British Pat. No. 1,080,904) and stirring for 6 hours at 20° C. The acetic acid produced as a result of desacetylation is neutralised in the pH range of 7.5–8.0 by adding 2 normal sodium hydroxide solution. The resulting desacetyl compound is left to stand in 150 ml of formic acid for 1½ hours at 22° C and thereby converted into the lactone. The mixture is evaporated, the residue is dissolved in 1 molar dipotassium hydrogen phosphate solution and the solution is washed with ethyl acetate. Acidification of the aqueous phase to pH 2.0, extraction with ethyl acetate and crystallisation from ethyl acetate-ether gives N-benzoyl-desacetyl-cephalosporin C-lactone, melting point 136°–138° C.

EXAMPLE 19

Analogously to Example 1, 3.3 g of 7β-(D-α-p-methoxybenzyloxycarbonylamino-α-phenylacetamido)-cephalosporanic acid in 170 ml of buffer-dimethylformamide, 9:1, are stirred with 3.3 g of aluminium amalgam for 1 hour at 45° C and pH 6. The mixture is washed with ethyl acetate-ether, 1:3, and finally extracted with ethyl acetate at pH 2.0. Crude 3-methylene-7β-(D-α-p-methoxybenzyloxycarbonylamino-α-phenylacetylamino)-cepham-4α-carboxylic acid is thus obtained. Thin layer chromatogram on silica gel: Rf (system 52): 0.57, Rf (system 100): 0.36.

The starting material is obtained as follows: 63 g of p-methoxybenzyloxycarbonyl-D-phenylglycine (obtained from chloroformic acid p-methoxybenzyl ester and D-phenylglycine) are dissolved in 700 ml of tetrahydrofurane and 27.4 ml of triethylamine and after addition of 26 ml of chloroformic acid isobutyl ester the mixture is stirred for 15 minutes at −10° C. A cold solution of 52 g of 7βaminocephalosporanic acid in 600 ml of tetrahydrofurane-water, 1:1, and 26 mi of diethylamine is added thereto. The whole is stirred for 1 hour at 0° C and 1 hour at 20° C. The mixture is concentrated, extracted with ethyl acetate at pH 2.0 and the product crystallised. 7β(D-α-p-Methoxybenzyloxycarbonylamino-α-phenylacetyamino)cephalosporanic acid is thus obtained; melting point 154°–155° C. Thin layer chromatogram: Rf (system 100): 0.42.

EXAMPLE 20

The amalgam from 1.6 g of aluminum is added to a suspension of 1.56 g of 7β-(D-α-tert.-butoxycarbonylaminophenylacetylamino)-cephalosporanic acid 1-oxide in 36 ml of 0.5 molar phosphate buffer (pH 7) and 4 ml of dimethylformamide and the mixture is stirred for 30 minutes at pH 6.0 an 45° C. Working up, carried out in accordance with Example 1, and crystallisation from ethyl acetate gives 3-methylene-7β-(D-α-tert.-butoxycarbonylamino-phenylacetylamino)-cepham-4α-carboxylic acid 1-oxide, melting point 222–5° C; thin layer chromatogram Rf (system 52): 0.33; Rf (system 100): 0.21.

The starting material is manufactured a follows:

A solution of 7.05 g of m-chloroperbenzoic acid in 25 ml of alcohol is added to a solution of 16 g of 7β-(D-α-tert.-butoxycarbonylamino-phenylacetylamino)-cephalosporanic acid in 160 ml of 95 percent strength alcohol at 0° C and the mixture is stirred for 1 hour at 0° C. The crystallisation which commences is completed by adding 100 ml of ether and yields 22 g of crude product. After recrystallisation from methanol/acetone, 7β-(D-α-tert.-butoxycarbonylamino-phenylactylamino)-cephalosporanic acid 1-oxide is obtained, melting point above 300° C; thin layer chromatogram Rf (system 52): 0.32; Rf (system 100): 0.27.

EXAMPLE 21

130 mg of m-chloroperbenzoic acid are added to a solution of 270 mg of 3-methylene-7β-(D-α-tert.-butoxycarbonylamino-phenylacetylamino)-cepham-4α-carboxylic acid in 25 ml of 95 percent strength ethanol and 5 ml of methanol and the mixture is stirred for 30 minutes at 22° C. Evaporation gives a crude product which is recrystallised from methanolacetone. 3-Methylene-7β(D-α-tert.-butoxycarbonylamino-phenylacetylamino)-cepham-4-carboxylic acid 1-oxide is obtained, melting point 225–6° C; $[\alpha]_b^{20} = -107° \pm 1°$ (C = 1,dimethylsulphoxide). The product is identical with the reduction product obtained in Example 20.

EXAMPLE 22

100 g (0.177 mol) of 7β-(D-α-tert.-butoxycarbonylamono-phenylacetylamino)-cephalosporanic acid ethanolamine salt are dissolved in a mixture of 2.2 l of doubly distilled water, 0.3 l of 1 M potassium phosphate buffer (pH 6.0), 0.4 l of methanol and 0.3 l of ethyl acetate. Amalgam prepared from 50 g of aluminium grit is added thereto and the mixture is adjusted to pH 6.7 by addition of concentrated phosphoric acid. This pH value is maintained constant during the entire reduction by adding further acid. The mixture is stirred vigorously for 1 hour at 35° C. To prevent heavy foaming, approx. 70 ml. of ethyl acetate are added gradually.

For working up, the mixture is poured onto 1.5 kg of ice and 1 l of ethyl acetate and is adjusted to pH 2.1 with approx. 220 ml of concentrated phosphoric acid. The excess amalgam is sieved off through a steel wire fabric and washed with 1.5 l of ethyl acetate. The phases of the filtrate which has been combined with the wash liquor are separated and the organic phase is washed twice, in each case with 1.5 l of ice water containing 4 ml of phosphoric acid. The aqueous phases are twice re-extracted with 2 l of ethyl acetate at a time. The combined ethyl acetate extract is dried over sodium sulphate, filtered and concentrated to approx. 300 g in vacuo. The incipient crystallisation is completed by cooling and slow addition of 460 ml of ethyl acetate-hexane, 2:3. The crystalline 3-methylene-7β-D-α-t-butoxycarbonylamino-phenylacetylamino)-cepham-4α-carboxylic acid is filtered off and washed with cold ethyl acetate-hexane, 7:3. The compound is identical with the compounds obtained according to Examples 1—3.

Further quantities of the desired acid can be obtained by evaporation of the filtrate and of the wash liquor and crystallisation of the residue, as previously.

EXAMPLE 23

4.67 g of the ethanolamine salt of 7β-phenoxyacetylamino-cephalosporanic acid are dissolved in a mixture of 104 ml of water (doubly distilled), 14 ml of 1 M potassium phosphate buffer (pH 6.5), 17ml of acetonitrile and 17 ml of methanol and the solution is stirred in the presence of amalgam prepared from 2.64 g of aluminium grit for 1 hour at 35° C and pH 6.7. The pH is kept constant by addition of concentrated phosphoric acid. On carrying out the reaction, working up and crystallisation analogously to Example 22, crytalline 3-methylene-7β-phenoxyacetylamino-cepham-4α-carboxylic acid is obtained, melting point 185°–188° C.

To prepare the starting material, a solution of 2.5 ml of ethanolamine in 12.5 ml of methanol is added to a solution of 15.6 g of 7β-phenoxyacetylamino-cephalosporanic acid in 50 ml of methanol and 25 ml of ether at −10° C and the crystal paste is filtered off after standing for a short time The crystalline ethanolamine salt of 7β-phenoxyacetylaminocephalosporanic acid is obtained, melting point 164° C.

EXAMPLE 24

0.05 ml of trimethylchlorosilane is added to a mixture of 45 mg of 3-methylene-7β-(D-α-tert,-butoxycarbonylaminophenylaceylamino)-cepham-4-carboxylic acid in 1 ml of pyridine and the clear solution is left to stand for 17 hours at 22° C. The solution is added to an ice-cold mixture of ethyl acetate and 5 percent aqueous phosphoric acid, the phases are separated and the ethyl acetate extract is dried over sodium sulphate and then evaporated. Pure 3-methyl-7β-(D-α-tert.-butoxycarbonylamino-phenylacetylamino)-ceph-3-em-4-carboxylic acid is obtained; thin layer chromatogram Rf (system 52): 0.67; Rf (system 100): 0.60.

EXAMPLE 25

Dry ampoules or phials containing 0.5 g of 3-methoxy-7β-(α-phenylacetylamino)-3-cephem-4-carboxylic acid is prepared as follows:

| Composition (for 1 ampoule or phial) | |
|---|---|
| 3-Methoxy-7β-(α-phenylacetyl-amino)-3-cephem-4-carboxylic acid | 0.5 g |
| Mannitol | 0.05 g |

A sterile aqueous solution of the 3-methoxy-7β-(α-phenylacetylamino)-3-cephem 4-carboxylic acid and the mannitol is subjected to freeze-drying under aseptic conditions in 5 ml ampoules or 5 ml phials and the ampoules or phials are sealed and tested.

EXAMPLE 26

Dry powders or phials, containing 0.5 g of the inner salt of 3-methoxy-7β-(D-α-phenylglycyl-amino)-3-cephem 4-carboxylic acid are prepared as follows:

| Composition (for 1 ampoule or phial) | |
|---|---|
| Inner salt of 3-methoxy-7β-(D-α-phenyl-glycyl-amino)-3-cephem-4-carboxylic acid | 0.5 g |
| Mannitol | 0.05 g |

A sterile aqueous solution of the inner salt of 3-methoxy-7β-(D-α-phenylglycyl-amino)-3-cephem-4-carboxylic acid and of the mannitol is subjected to freeze-drying under aseptic conditions in 5 ml ampoules or 5 ml phials and the ampoules or phials are sealed and tested.

What we claim is:

1. Process for the manufacture of α-7β-amino-3-methylene-cephem-4-carboxylic acid compounds of the formula

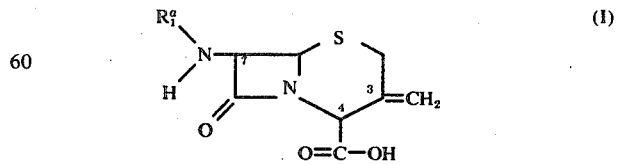

where $R_1^a$ represents hydrogen or 5-aminoadipoyl, wherein amino may be protected by benzoyl, or an acyl group of the formula

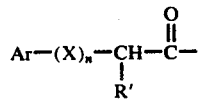
(B), wherein Ar represents phenyl, hydroxyphenyl or hydroxychlorophenyl, thienyl, or furyl, X represents oxygen $n$ represents 0 or 1 R' represents hydrogen or, if $n$ represents O, R' represents amino, amino protected by α-polybranched lower alkoxycarbonyl or p-methoxybenzyloxycarbonyl, 1-oxide thereof, or a salt of such compound which consists essentially of reducing a 7β-amino-3-acyloxymethyl-3-cephem-4-carboxylic acid compound of the formula (III)

wherein $R_1{}^a$ has the above-mentioned meaning, R denotes acetoxy, $R_2{}^o$ is hydroxyl or R and $R_2{}^o$ together denote an epoxy group, a 1-oxide thereof or a salt of such a compound, with an amalgam of aluminum at a pH of 2 to 7, in the presence of water at a temperature of between 0° to 100°.

2. Process according to claim 1, characterised in that a starting substance of the formula III, wherein $R_1{}^a$ represents hydrogen, 5-benzoylamino-adipoyl or an acyl group of the formula (B), wherein Ar is phenyl, X is oxygen, $n$ is 0 or 1 and R' is hydrogen or, if $n$ is 0, amino or amino protected by α-poly-branched lower alkoxycarbonyl or 4-methoxybenzyloxycarbonyl, R represents acetoxy $R_2{}^o$ represents hydroxyl, or R and $R_2{}^o$ together represent an epoxy group, the 1-oxide thereof, or a salt of such a compound, is used.

3. Process according to claim 1, characterised in that the starting material of the formula III which is used is 7β-(D-α-tert.-butoxycarbonylamino-α-phenylacetylamino)-cephalosporanic acid, 7β-(-phenylacetylamino)-cephalosporanic acid, 7β-aminocephalosporanic acid, N-benzoyl-cephalosporin, C, N-benzoyldesacetyl-cephalosporin C-lactone, 7β-(D-α-p-methoxybenzyloxycarbonylamino-α-phenylacetamino)cephalosporanic acid, 7β-(D-α-tert,-butoxycarbonylamino-phenylacetylamino)-cephalosporanic acid 1-oxide, 7β-phenoxyacetylamino-cephalosporanic acid or a salt of the acids mentioned.

4. Process according to claim 1, characterised in that the starting material used is an alkali metal salt or a hydroxy-lower alkylamino salt of an acid of the formula III.

5. Process according to claim 1, characterised in that aluminum grit amalgamated by means of mercury-(II) chloride or mercury-(II) acetate is used.

6. Process according to claim 1, characterised in that the pH value is adjusted to 6–7, by adding a water-soluble organic or inorganic acid.

7. Process according to claim 1, characterised in that the reduction is carried out in the presence of anions of hydrofluoric acid, oxalic acid, tartaric acid, citric acid, metaphosphoric acid, ethylenediaminetetraacetic acid, hydrogen sulphide of phosphoric acid.

8. Process according to claim 1, characterised in that the reduction is carried out in the presence of one or more organic solvents containing at least 10 to 20% of water.

9. Process according to claim 1, characterised in that the reduction is carried out in the presence of dimethylformamide, methanol, acetonitrile or ethyl acetate.

10. Process according to claim 1, characterised in that the reduction is carried out at temperatures between about 25° and 50° C.

* * * * *